US009132029B2

(12) United States Patent
Liang

(10) Patent No.: US 9,132,029 B2
(45) Date of Patent: *Sep. 15, 2015

(54) WARMER DEVICE AND ITS OPERATIONAL METHOD

(76) Inventor: ShengQuan Liang, Foshan (CN)

( * ) Notice: Subject to any disclaimer, the term of this patent is extended or adjusted under 35 U.S.C. 154(b) by 311 days.

This patent is subject to a terminal disclaimer.

(21) Appl. No.: 13/573,287

(22) Filed: Sep. 6, 2012

(65) Prior Publication Data

US 2013/0028578 A1     Jan. 31, 2013

Related U.S. Application Data

(62) Division of application No. 11/895,439, filed on Aug. 23, 2007, now Pat. No. 8,288,691, and a division of application No. 11/998,707, filed on Nov. 29, 2007.

(30) Foreign Application Priority Data

Jun. 4, 2007     (CN) .......................... 2007 1 0074814

(51) Int. Cl.
*H05B 3/34*     (2006.01)
*F24H 7/00*     (2006.01)
*A61F 7/00*     (2006.01)

(52) U.S. Cl.
CPC ......... *A61F 7/007* (2013.01); *A61F 2007/0086* (2013.01)

(58) Field of Classification Search
CPC ............ A61F 2007/0086; A61F 7/007; A61F 2007/0091

USPC ................. 219/523, 528, 529, 530, 538–549; 392/339–341

See application file for complete search history.

(56) References Cited

U.S. PATENT DOCUMENTS

| 2,310,723 | A  | * | 2/1943  | Whitchurch ................. 99/337 |
| 2,924,167 | A  | * | 2/1960  | Rhodes ........................ 99/337 |
| 6,222,160 | B1 | * | 4/2001  | Remke et al. ................ 219/387 |
| 8,288,691 | B2 | * | 10/2012 | Liang ........................... 219/528 |
| 8,288,692 | B2 | * | 10/2012 | Liang ........................... 219/528 |

* cited by examiner

*Primary Examiner* — Sang Y Paik
(74) *Attorney, Agent, or Firm* — Raymond Y. Chan; David and Raymond Patent Firm.

(57) ABSTRACT

A warmer device includes a rechargeable warmer bag containing liquid, a protection device for disposing the rechargeable warmer bag thereat, a charging unit for charging the rechargeable warmer bag to heat up liquid at a usable temperature, and a monitoring device for monitoring the rechargeable warmer bag, wherein the monitoring device includes an actuator operatively linked to the charging device and arranged in such a manner that the actuator is switched on to ensure the heating unit being operated to heat up the liquid, wherein the actuator is actuated by the bag when the bag is expanded, such that the actuator is switched off in response to an expansion of the bag at the protection device to cut off a power supply of the charging unit for preventing the bag being over-expanded.

24 Claims, 27 Drawing Sheets

WARMER DEVICE AND ITS OPERATIONAL METHOD

CROSS REFERENCE OF RELATED APPLICATION

This is a Divisional application that claims the benefit of priority under 35 U.S.C. §119 to a first non-provisional application, application Ser. No. 11/895,439, filed Aug. 23, 2007 now U.S. Pat. No. 8,288,691, and a second non-provisional application, application Ser. No. 11/998,707, filed Nov. 29, 2007.

BACKGROUND OF THE PRESENT INVENTION

1. Field of Invention

The present invention relates to a warmer device, and more particularly to a warmer device and operating method thereof, wherein the warmer device comprises a protection device, a rechargeable warmer bag, and a monitoring device, wherein the rechargeable warmer bag comprises a bag, a heating unit, a charging unit and the monitoring device is arranged in the protection device with respect to the rechargeable warmer bag so that the rechargeable warmer bag is monitored and control by the monitoring device while the rechargeable warmer bag is being charged in the cavity of the protection device. Therefore, when the rechargeable warmer bag is heated to be over expanded, the monitoring device cuts the power supply of charging unit of the rechargeable warmer bag. However, when the rechargeable warmer bag is being used, the rechargeable warmer bag and the monitoring device are separated.

2. Description of Related Arts

During winter time, most people would like to use some warmer apparatus, such as electric heaters, in order to keep themselves warm. However, such warmer apparatus requires an electric power and has a relatively bulky size that the user cannot carry the warmer apparatus everywhere.

As everyone knows, it is very cold in winter, so people have invented various kinds of warmer device to keep warm in cold days. Some kinds of warmer device are huge, and inconvenient to carry out.

There is a kind of small and portable warmer device, called warm water bag comprising a bag and a sealing cover, wherein the bag is made of water proof material such as plastic. The bag has an inner cavity and an opening, and the sealing cover is to cover the opening. In order to use it, the user has to heat a certain amount of liquid, such as water in a stove or other devices, and fill the warm liquid into the inner cavity of the bag. At last, cover the sealing cover onto the opening to seal the cavity so as to keep the liquid inside. Therefore, the user is able to hold the bag close to the body of the user. In other words, the water inside the cavity gradually dispenses its heat through the sealing bag, so that the user can put the bag to part of body, such as hands or feet, to keep himself or herself warm.

The warm water inside the cavity conducts or radiate the heat to the outside constantly, so that the user can put the warm water bag to part of body where is cold, such as hands or feet to keep warm.

However, an essential disadvantage of the traditional warm water bag is inconvenient to use. Since the liquid radiate its heat, the temperature is decreasing at the same time. The warm water bag can no longer provide heat when the temperature drops down to a level similar to the body temperature. The user has to pour out the liquid in the cavity and refill warm water repeatedly. It is very inefficient and inconvenient.

Some inventors create a kind of rechargeable warmer bag, comprising a bag, a power supply unit, and a warmer device, wherein the bag has a cavity with a predetermined amount of liquid therein and the warmer device which is positioned in the cavity of the bag comprises a heating tube and a socket connecting to the power supply unit.

In order to use the rechargeable warmer bag, connect it to the power supply, so that the electricity is converted to heat in the heating tube and the heating tube conducts heat to the liquid in the cavity. After a certain time, the liquid is warm enough, the user cuts off the power supply to use the rechargeable warmer bag.

But, as mentioned above, the liquid in the cavity will expand when the rechargeable warmer bag is being charged. The higher the temperature, the more it expands. When it expands too much, the pressure in the bag is rising. As the pressure is rising to a certain extent, the bag will be broken and the hot liquid inside will be leaked or even sprayed out. If this is happened, the conventional rechargeable warmer bag contains safety problems and causes dangerous to the user's life. This is a main disadvantage of the rechargeable warmer bag.

An improved water bag is made that the water bag is adapted to be placed in a microwave oven to heat up the water inside the water bag. Likewise, a built-in heating element is mounted into the water bag to heat up the water inside the water bag.

However, the traditional water bag is inconvenient for people to use. Since the hot water is gradually cooling down in a timely manner, the water bag cannot provide the warming ability after a short period of time. Then, the user must pour out the water inside the sealing bag and refill the hot water. In other words, the user must repeatedly refill the hot water frequently, which is very inefficient and inconvenient.

In the other hand, it is convenient for the user to heat up the water inside the sealing bag by microwave oven. However, it is relatively dangerous for the user when the water inside the sealing bag is overheated. Accordingly, few seconds of contacting with the hot water will cause a serious burn. The overheated water inside the sealing bag will also cause a serious explosion.

Likewise, by electrically connecting the heating element with the external power source, the water inside the sealing bag can be gently heated up by the heating element. However, when the water is heated, the volume of the water is expanded. When the water expands at a predetermined volume larger than the capacity of the sealing bag, the sealing bag will be forced to be popped and the hot water will be leaked from the sealing bag. Since the heating element is electrically connected to the power source, the hot water leaking from the sealing bag may cause an electrical short circuit or even a serious electric shock to the user. In other words, the user needs to find more secure and safe way to keep warm by using the water bag.

SUMMARY OF THE PRESENT INVENTION

A main object of the present invention is to provide a warmer device and operating method thereof, wherein the special design is a breakthrough of traditional warmer device.

Another object of the present invention is to provide a warmer device and operating method thereof, which is designed to be convenient and portable.

Another object of the present invention is to provide a warmer device and operating method thereof, which is designed to assure its operation safety.

Another object of the present invention is to provide a portable warmer, wherein the heating operation for the warmer bag is monitored by the safety arrangement to prevent the fluid inside the bag from being overheated.

Another object of the present invention is to provide a portable warmer, wherein the warmer bag is small and portable for people to use.

Another object of the present invention is to provide a portable warmer, wherein the warmer bag provides two different security apparatus to guarantee its using safety.

Another object of the present invention is to provide a portable warmer, which does not require to alter the original structural design of the warmer bag, so as to minimize the manufacturing cost of the warmer bag incorporating with the casing.

Another object of the present invention is to provide a portable warmer, wherein no expensive or complicated structure is required to employ in the present invention in order to achieve the above mentioned objects. Therefore, the present invention successfully provides an economic and efficient solution for providing a safety configuration for the portable warmer to prevent the fluid inside the warmer bag from being overheated.

Accordingly, in order to accomplish the above object, the present invention provides a warmer device, comprising:

a protection device having a protection cavity therein; and a rechargeable warmer bag arranged to be charged in the protection device in such a manner that the rechargeable warmer bag is disposed in the protection cavity of the protection device during charging and the rechargeable warmer bag is removed from the protection device for use.

The rechargeable warmer bag comprises:

a bag, having an outer surface and an inner surface defining a sealed cavity receiving a predetermined amount of liquid therein;

a heating unit which is disposed in the liquid in the sealed cavity of the bag comprising a plurality of heaters;

a charging unit, which is connected with the heating unit and disposed between the bag and the heating unit, comprising a charging connector and a connecting wire; and a monitoring device arranged in the protection device with respect to the rechargeable warmer bag so as to monitor the rechargeable warmer bag and cut off the power supply of the charging unit of the rechargeable warmer bag when the rechargeable warmer bag is over-expanded, and that when the rechargeable warmer bag is in use, the rechargeable warmer bag and the monitoring device are separated.

Therefore, the rechargeable warmer bag must be placed in the cavity of the protection device during charging. At this moment, the rechargeable warmer bag is monitored and control by the monitoring device. If the rechargeable warmer bag is heated to be expanded to a certain extent, the rechargeable warmer bag will be in contact with the actuator and the actuator disconnects the external circuit to protect said rechargeable warmer bag from being broken or exploded. When the rechargeable warmer bag is being used, the rechargeable warmer bag is disconnected with the monitoring device.

In accordance with another aspect of the invention, the present invention provides a warmer bag comprises:

a casing having a receiving compartment;

a warmer bag comprising a bag body defining a fluid cavity therein, and a heat exchanging fluid sealed and contained in the fluid cavity of the bag body;

a heating arrangement comprising a power cable having a power outlet extended out of the casing for electrically connecting with an external power source and a power adapter extended into the receiving compartment, an electric terminal provided at the bag body, and a heating element which is supported in the fluid cavity and is electrically coupled with the electric terminal, wherein when the warmer bag is disposed in the receiving compartment, the power adapter of the power cable is detachably and electrically coupled with the electric terminal for electrically connecting the heating element with the external power source so as to heat up the heat exchanging fluid at a predetermined usable temperature; and a safety arrangement electrically coupling with the heating arrangement, wherein when the heat exchanging fluid is heated above the usable temperature, the safety arrangement automatically cuts off an electrical connection between the heating element and the external power source for preventing the heat exchanging fluid from being overheated.

Accordingly, the safety arrangement comprises a contact switch provided at the casing such that when the warmer bag is disposed in the casing during the heating operation, the contact switch is automatically actuated to cut off the electrical connection between the heating element and the external power source in responsive to the expansion of the heat exchanging fluid.

These and other objectives, features, and advantages of the present invention will become apparent from the following detailed description, the accompanying drawings, and the appended claims.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
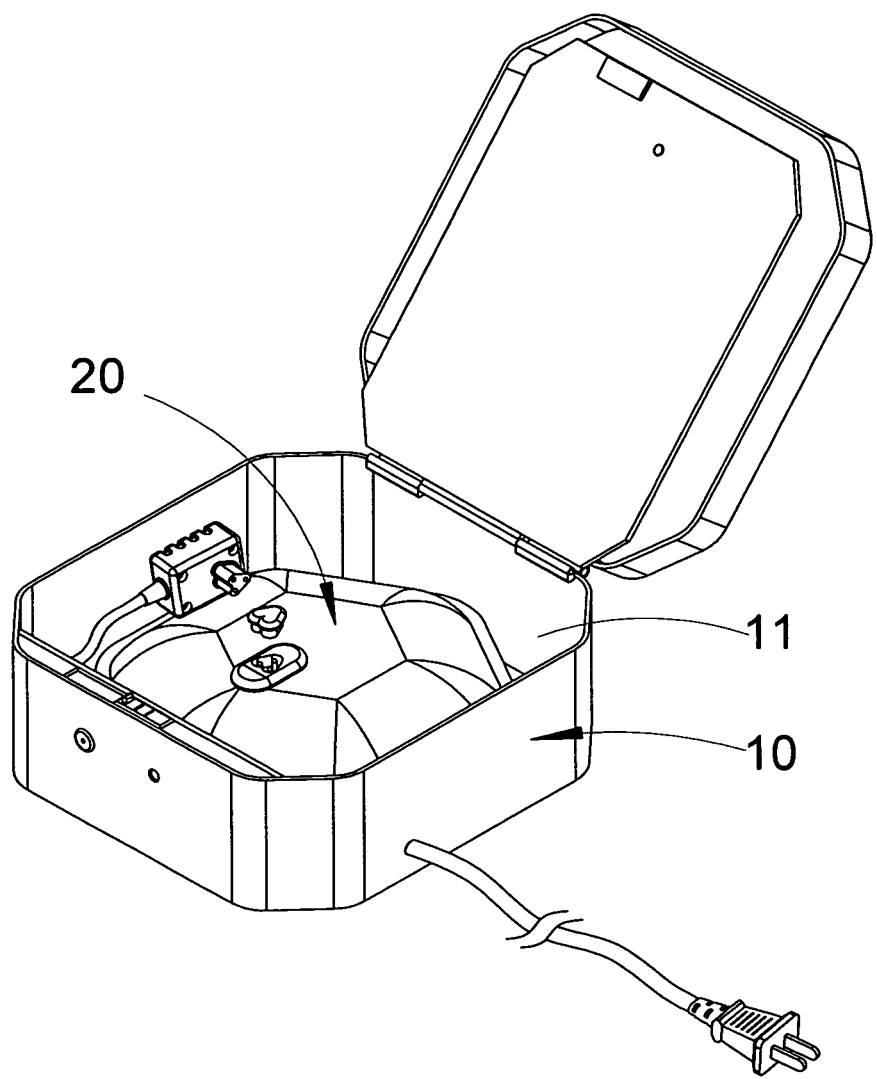
FIG. 1 is a perspective view of a charge warmer device according to a preferred embodiment of the present invention.
Figure 2:
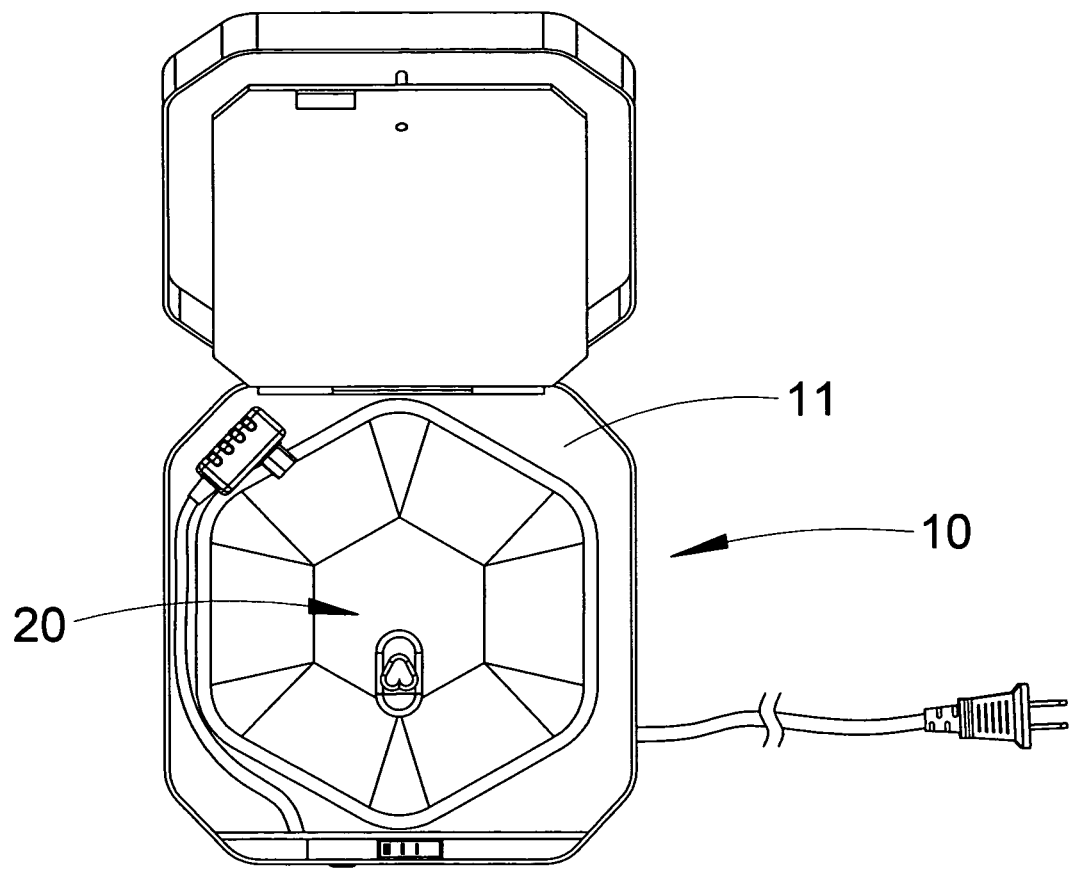
FIG. 2 is a top exterior view of the charge warmer device according to the above preferred embodiment of the present invention.
Figure 3:
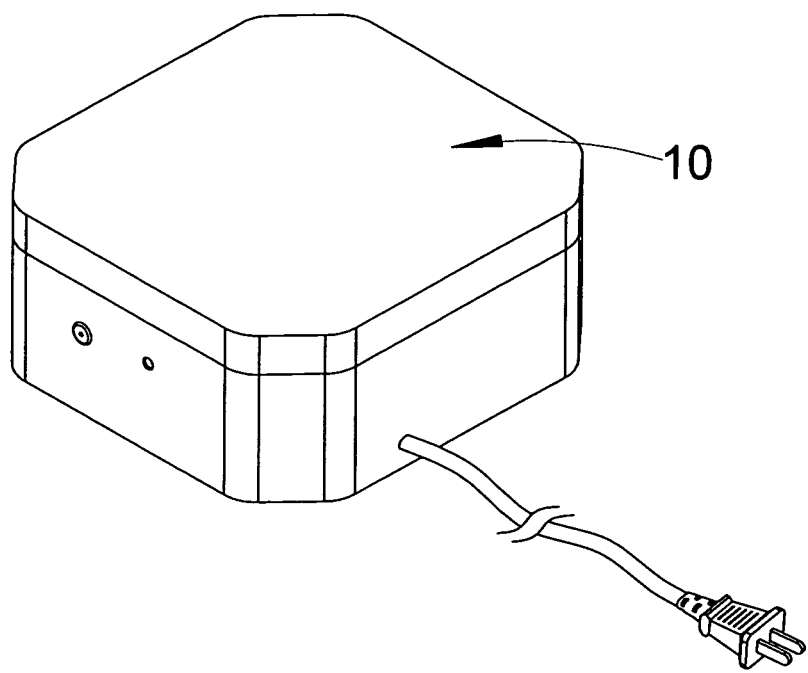
FIG. 3 is a perspective view of the charge warmer device at a closed position according to the above preferred embodiment of the present invention.
Figure 4:
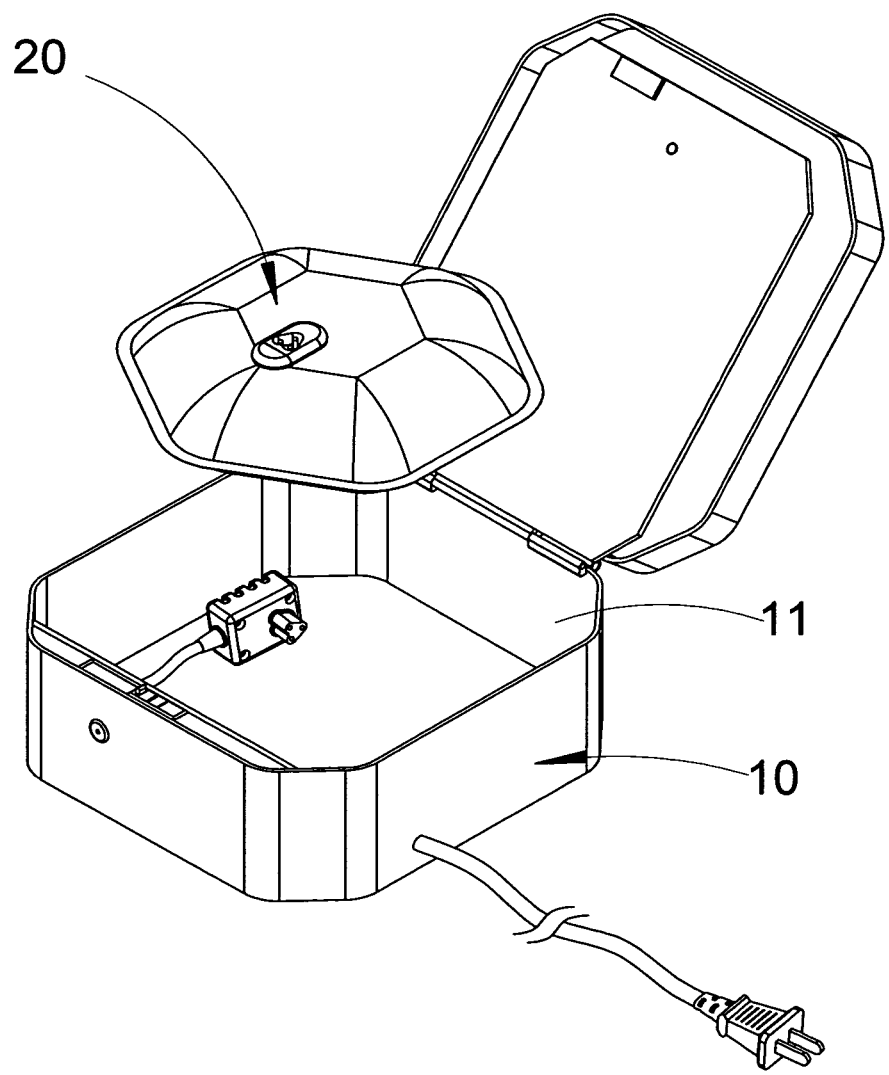
FIG. 4 is an exploded view of the charge warmer device according to the above preferred embodiment of the present invention.
Figure 5:
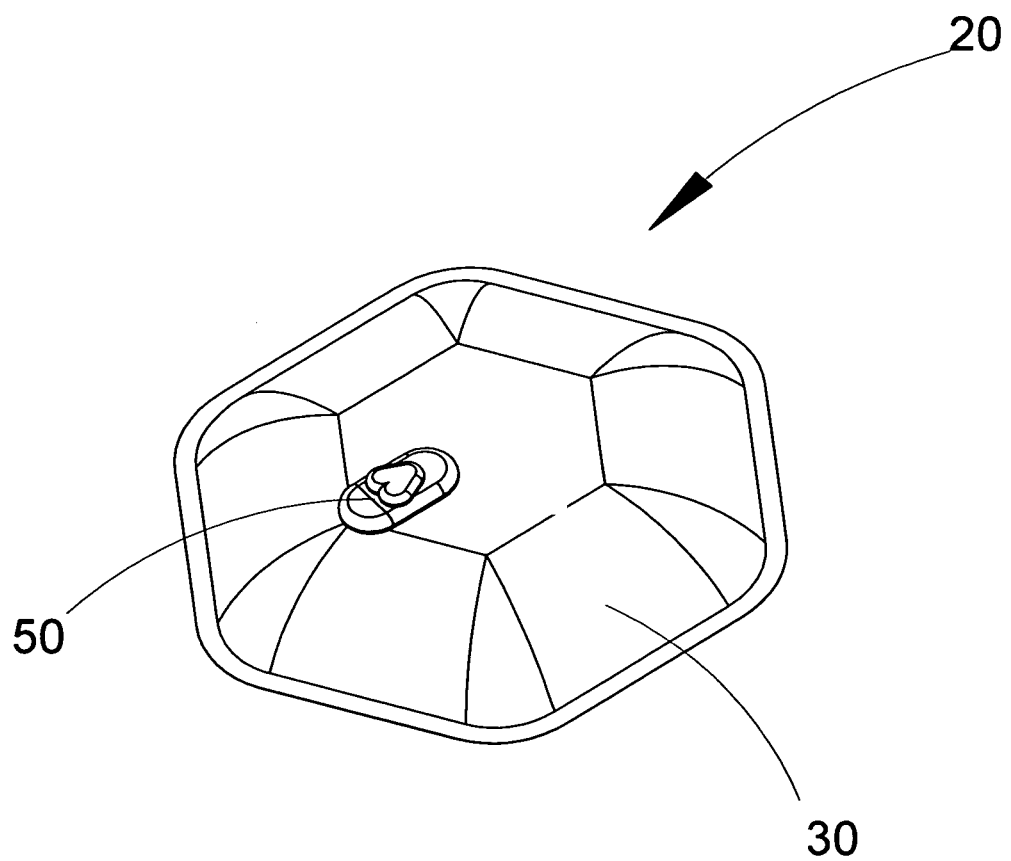
FIG. 5 is a perspective view of a rechargeable warmer bag according to the above preferred embodiment of the present invention.
Figure 6:
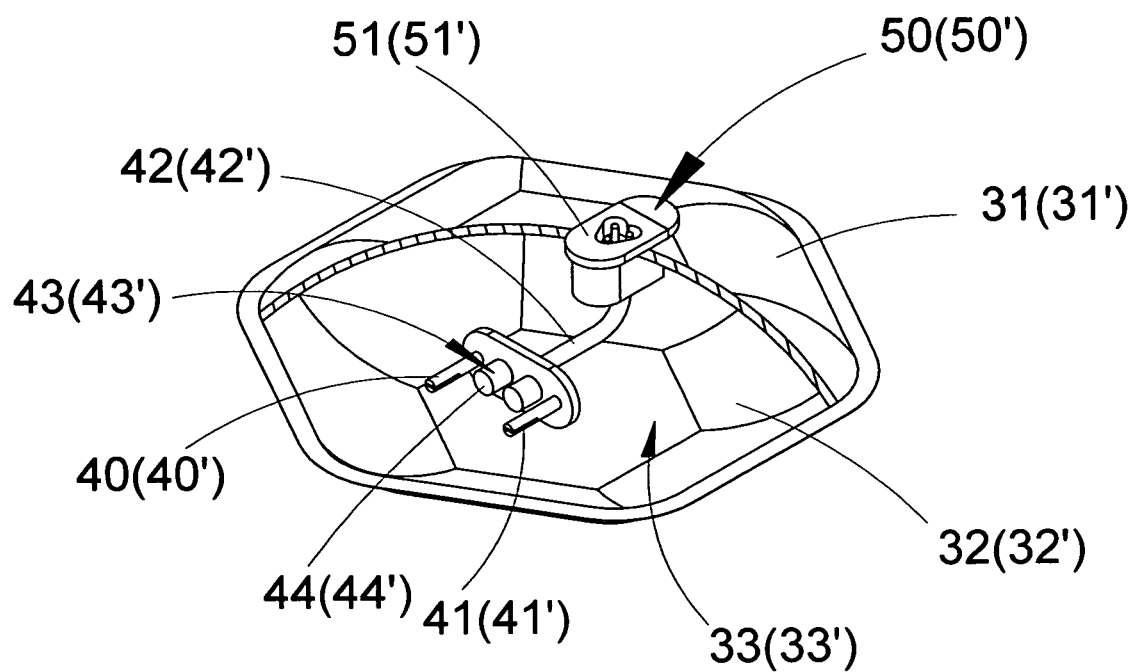
FIG. 6 is a schematic view of the rechargeable warmer bag according to the above preferred embodiment of the present invention.
Figure 7:
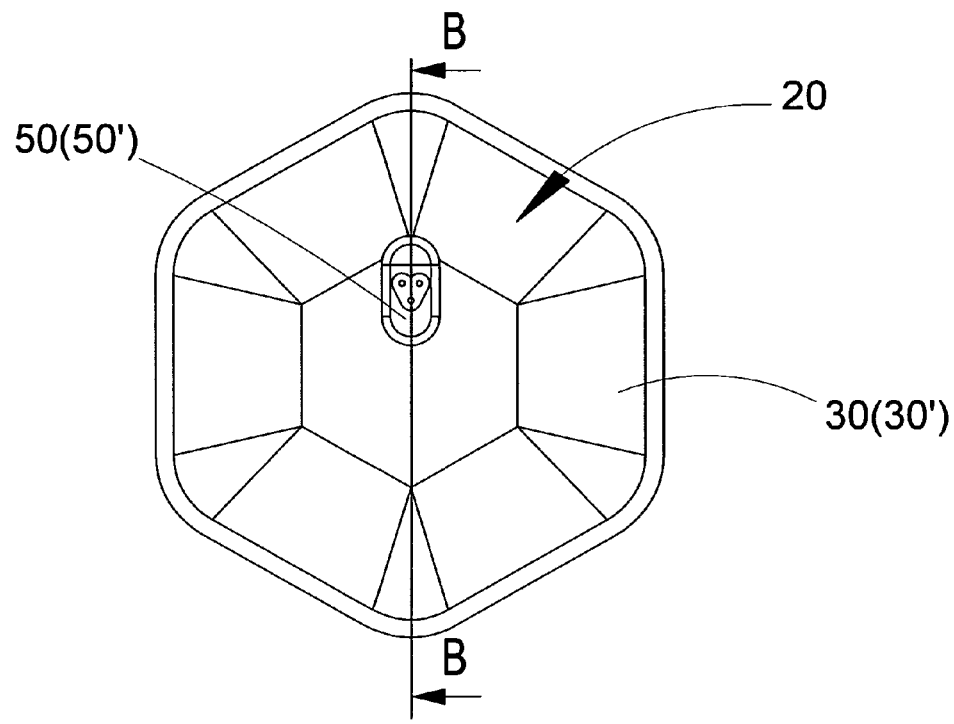
FIG. 7 is a top exterior view of the rechargeable warmer bag according to the above preferred embodiment of the present invention.

Referring to FIG. 1 to FIG. 4 of the drawings, a warmer device according to a preferred embodiment of the present invention is illustrated. The warmer device comprises a protection device 10 having an interior protection cavity 11 isolated from outside environment and a rechargeable warmer bag 20 arranged to be charged in the protection device 10.

The rechargeable warmer bag 20 is disposed in the cavity 11 of the protection device 10 during charging and removed out of the protection device 10 during operation thereof.

As shown in FIG. 5 to FIG. 8, the rechargeable warmer bag 20 further comprises:

a bag 30 having an outer surface 31 and an inner surface 32 defining a sealed cavity 33 receiving a predetermined amount of liquid 34 therein;

a heating unit 40 which is disposed in the liquid 34 in the sealed cavity 33 of the bag 30 comprising a plurality of heaters 41;

a charging unit 50, which is connected with the heating unit 40 and positioned between the bag 30 and the heating unit 40, comprising a charging connector 51 and a connecting wire; and a monitoring device 60 arranged in the protection device 10 with respect to the rechargeable warmer bag 20 so as to monitor the rechargeable warmer bag 20 and cut off the power supply of the charging unit 50 of the rechargeable warmer bag 20 when the rechargeable warmer bag 20 is over-expanded, and that when the rechargeable warmer bag 20 is in use, the rechargeable warmer bag 20 and the monitoring device 60 are separated.

As shown in FIG. 9 to FIG. 12, the protection device 10 comprises a box 12 and a box cover 13 for covering the box 12, wherein the box 12 has an outer surface 122 and an inner surface 121 defining a cavity 123 separated from the outer space by the box cover 13.

The protection device 10 further comprises a pivot 14 for pivotally connecting the box 12 and the box cover 13.

The protection device 10 further comprises a buckle 15 between the box 12 and the box cover 13 for securing the box cover 13 on the box 12 so as to separate the cavity 123 of the box 12 from the outer space.

The rechargeable warmer bag 20 should be placed in the cavity 123 of the protection device 10 when being charged.

Figure 13:
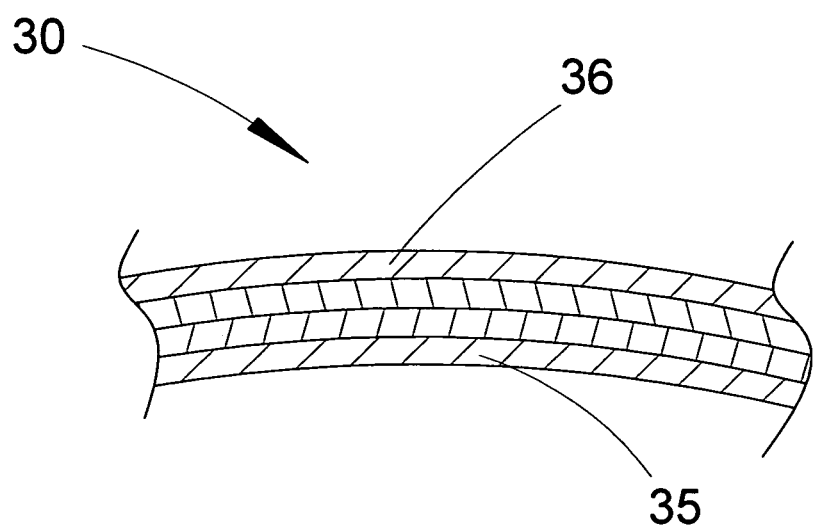
FIG. 13 is a schematic view of the bag according to the above preferred embodiment of the present invention.

The bag is made of a water-proof material. Furthermore, the bag is made of a soft water-proof material. As shown in FIG. 13, the bag 30 comprises a plurality of layers, wherein the innermost layer 35 is made of water-proof material that can seal the liquid 34 within the sealed cavity 33 of the bag 30, and the outermost layer 36 is made of soft material so as to be touched by the user skin.

Figure 8:
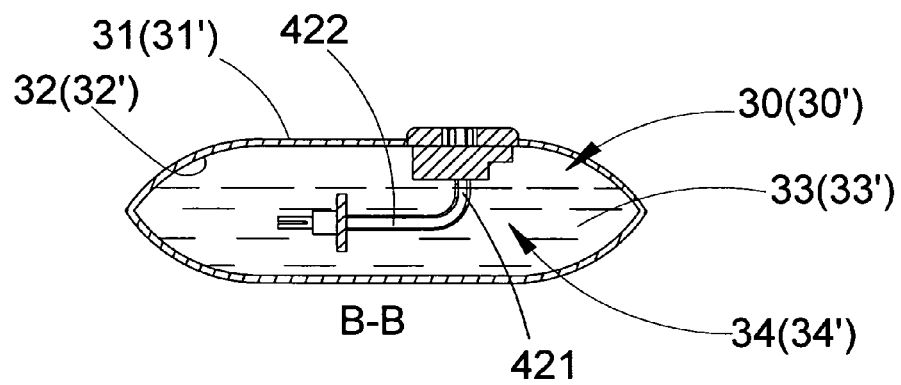
FIG. 8 is a B-B sectional view of the rechargeable warmer bag according to the above preferred embodiment of the present invention.

As shown in FIG. 8, the heating unit 40 in the bag 30 further comprises a connecting tube 42 and the temperature control device 43.

The temperature control device 43, which is connected between the heaters of the heating unit 40, comprises a plurality of temperature controllers 44 with different rated temperature for cutting off the power supply. The temperature control device 43 monitors the temperature of the liquid 34 in the bag 30 in real-time during the rechargeable warmer bag 20 is being charged. When the temperature is up to the rated temperature of any temperature controller 44, the temperature control device cuts off the power supply of the charging unit 50.

The following is one of the temperature safety protection arrangements according to the present invention.

The connecting tube 42 is securely connected between the heaters 41 and the charging connector 51 of the charging unit 50 so as to support the heaters 41 to be positioned within the sealed cavity 33 of the bag 30. When the rechargeable warmer bag 20 is being charged, the connecting tube 42 supports the heaters to ensure that the heaters are disposed in the sealed cavity 33 of the bag 30 and surrounded by the liquid 34 in the cavity 33.

As the heater 41 of the heating unit 40 converts the electricity to the heat, and conducts the heat to the liquid 34 in the bag 30, the temperature of the liquid 34 raises and the volume of the liquid 34 is expanded. At this moment, the gas generated inside the bag 30 is expanded too. According to the proportional relation of the gas expansion and liquid expansion when heated, the gas expansion velocity is faster than liquid expansion velocity, so that the gas in the cavity squeezes liquid 34 in the cavity. Gradually, the heater 41 of the heating unit 40 separates from the liquid 34, as the liquid level falls due to the rising of the liquid temperature, and then the charge warmer device 20 is cut off from the power supply.

The following is another temperature safety protection arrangement according to the present invention.

Furthermore, the connecting tube 42 comprises a vertical tube 421 and a transverse pole 422.

The charging connector 51 of the charging unit 50 can be embodied as a socket.

Figure 14:
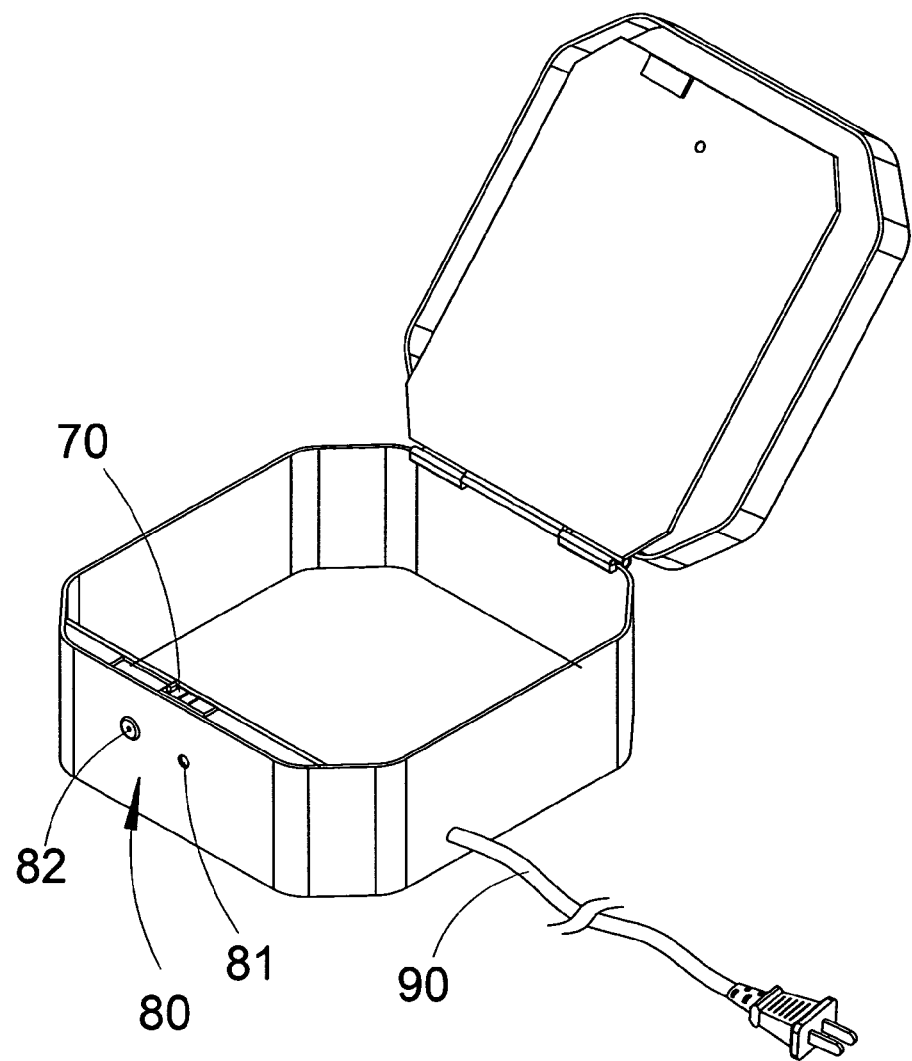
FIG. 14 is a schematic view of a monitoring device of the protection device according to the above preferred embodiment of the present invention.
Figure 15:
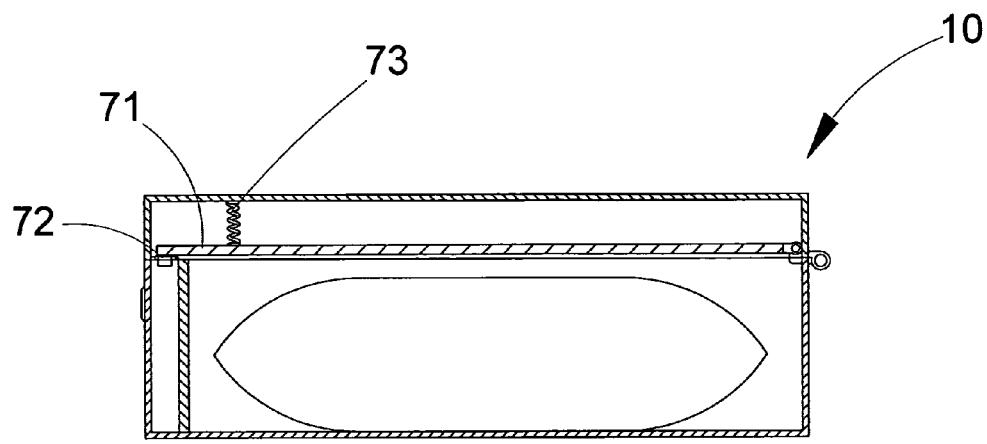
FIG. 15 is a schematic view of a protection device with a rechargeable warmer bag therein according to the above preferred embodiment of the present invention
Figure 16:
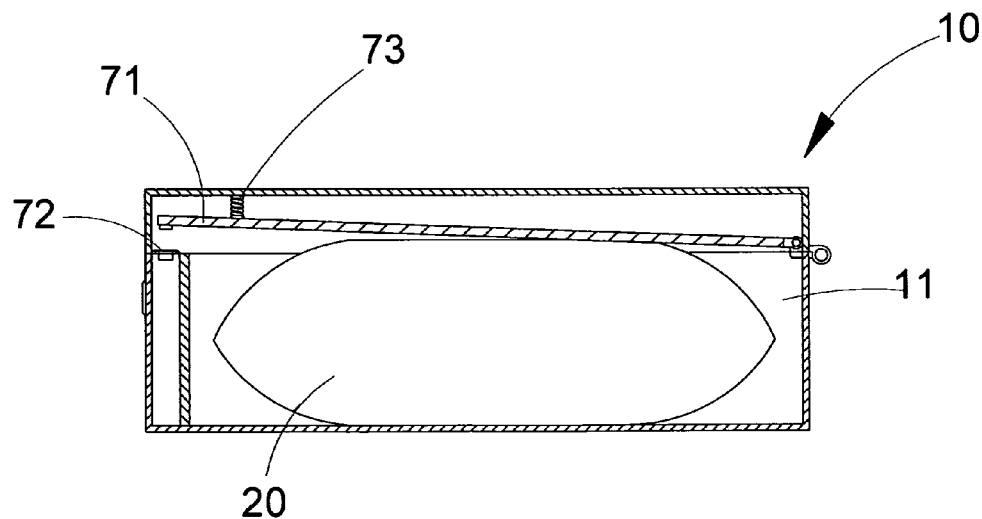
FIG. 16 is a schematic view of a protection device with an expanded rechargeable warmer bag according to the above preferred embodiment of the present invention.
Figure 17:
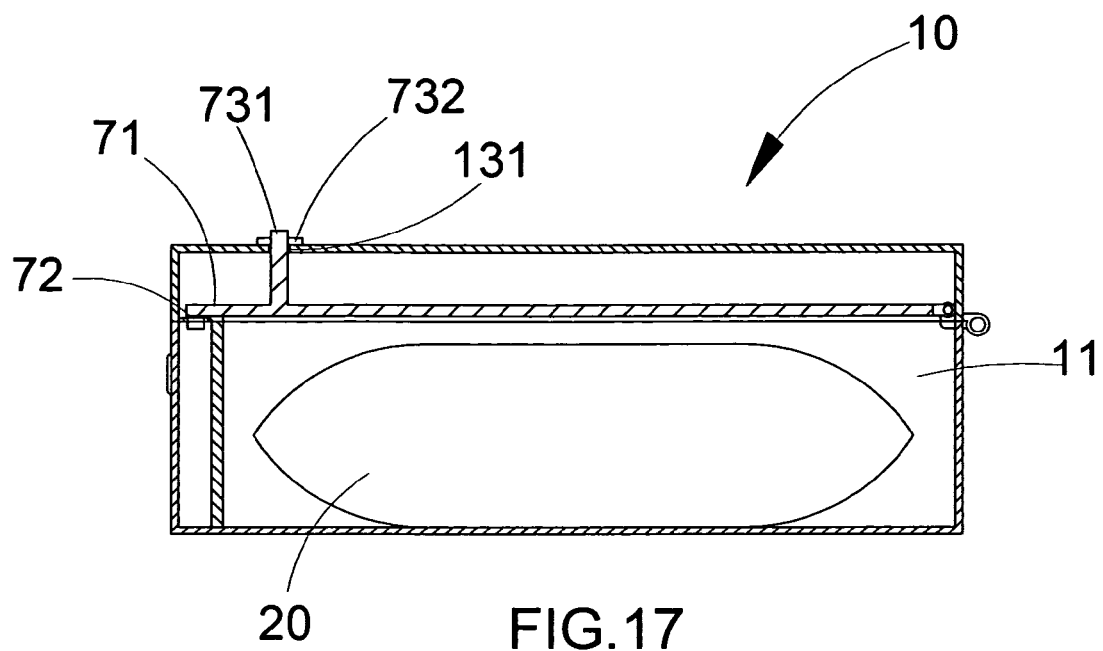
FIG. 17 is a schematic view of a protection device with a rechargeable warmer bag therein according to the above preferred embodiment of the present invention.
Figure 18:
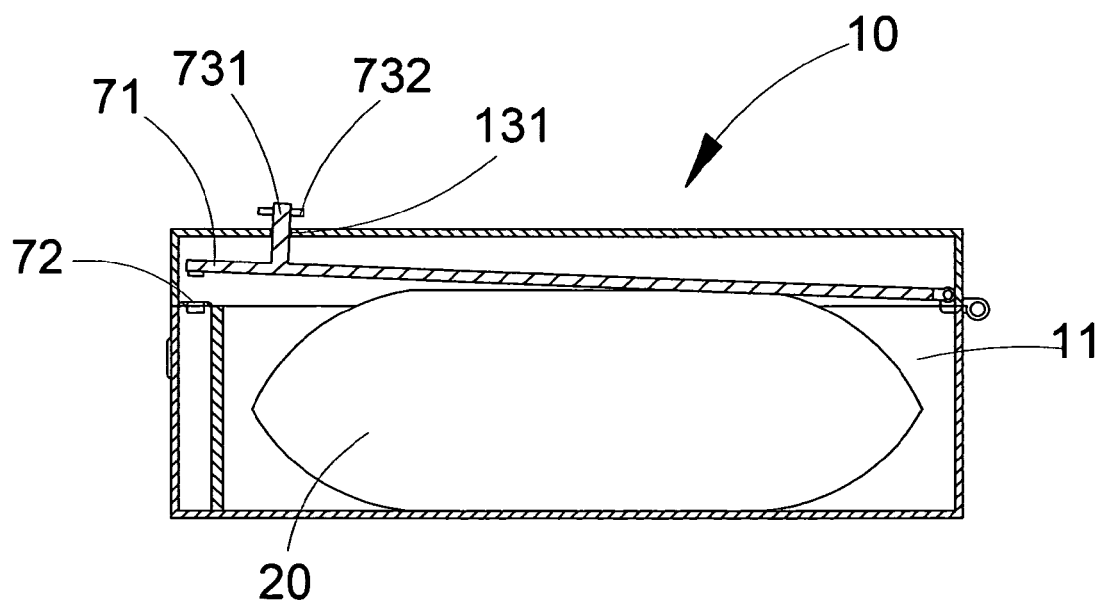
FIG. 18 is a schematic view of a protection device with an expanded rechargeable warmer bag according to the above preferred embodiment of the present invention.

As shown in FIG. 14, the monitoring device 60 disposed in the cavity 11 of the protection device 10 comprises an actuator 70, an altering device 80, and an external circuit 90.

As shown in FIG. 15 to FIG. 18, the actuator 70 is connected to the external circuit 90 and disposed in the cavity 11. When the rechargeable warmer bag 20 is being charged in the cavity 11 of the protection device 10, the rechargeable warmer bag 20 is monitored and controlled by the monitoring device 60. If the rechargeable warmer bag 20 is heated to be over-expanded, the rechargeable warmer bag 20 will be in contact with actuator 70 and then the actuator 70 disconnects the external circuit 90 so as to protect the rechargeable warmer bag 20 from being broken or explosion.

The actuator 70 comprises an actuator board 71, an actuator switch 72 and a connecting element 73, wherein the actuator board 71 is disposed in the cavity 11 of the protection device 10 and placed above the rechargeable warmer bag 20 when being charged in the cavity 11 of the protection device.

Furthermore, the actuator board 71 is placed in the box cover 13 of the protection device 10.

One end of the actuator board 71 is pivotally connected to the top of the protection device 10.

In addition, the actuator switch 72 and the connecting element 73 are provided on the other end of the actuator board 71 and the actuator switch 72 is connected to the external circuit 90.

The connecting element 73 can be embodied as an elastic element, such as a spring, which is connected to the box cover 13 of the protection device 10. When the rechargeable warmer bag 20 is over expanded during charging in the protection device 10, the bag 30 is expanded upward to touch the actuator board 71 and the connecting element 73 on the other end of the actuator board 71 is compressed. And then the actuator switch 72 disconnects with the external circuit 90 to cuts off power supply so as to stop charging the rechargeable warmer bag 20 to avoid the over expansion of the bag 30.

Alternatively, the connecting element 73 can be embodied a hard connecting pole, comprising a fixed pole 731 and a retaining sheet 732. The box cover 13 of the protection device 10 has a through hole 131 therein for receiving the fixed pole 731. The retaining sheet 732 is positioned on the top of the fixed pole 731, bigger than the through hole 131 in size.

As mentioned above, the connecting element 73 comprises a plurality of elastic elements, each having one end connected to the top of the protection device 10 and another end connected to the actuator board 71. When the rechargeable warmer bag 20 is being charged in the cavity 11 of the protection device 10, the actuator board 71 is positioned on the upper side of the protection device relative to the rechargeable warmer bag 20.

The actuator switch 72 is positioned on the actuator board 71, and connects to the external circuit 90.

Furthermore, the elastic element is embodied as a spring.

Figure 19:
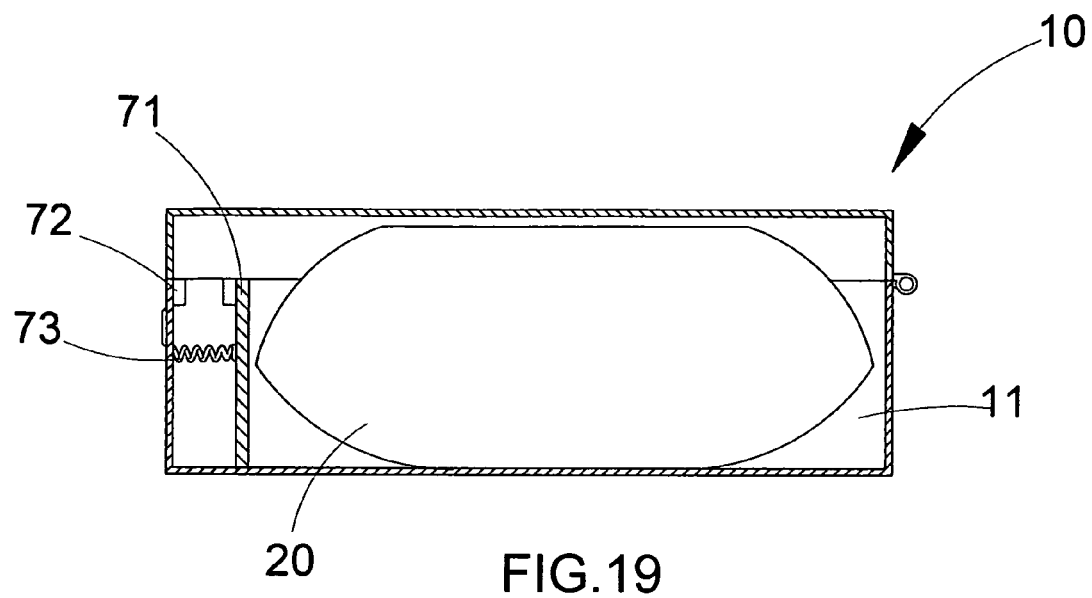
FIG. 19 is a schematic view of a protection device with a rechargeable warmer bag therein according to the above preferred embodiment of the present invention.
Figure 20:
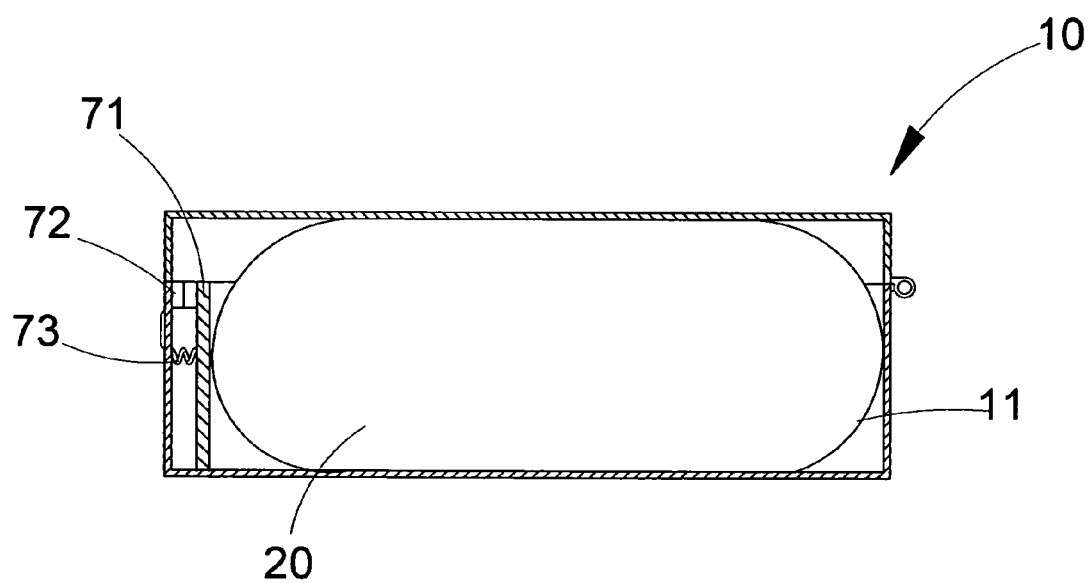
FIG. 20 is a schematic view of a protection device with an expanded rechargeable warmer bag according to the above preferred embodiment of the present invention.

As shown in FIG. 19 to FIG. 20, the actuator 70 comprises an actuator board 71 disposed in the cavity 11 of the protection device 10, an actuator switch 72, and a connecting element 73. When the rechargeable warmer bag 20 is being charged in the cavity 11 of the protection device 10, the actuator 71 is positioned surrounding the rechargeable warmer bag 20 and the actuator switch 72 is positioned between the actuator board 71 and the external circuit 90.

The connecting element 73 is connected with the side wall of the protection device. If rechargeable warmer bag 20 is heated to be over expanded during charging in the protection device 10, the bag 30 expands to touch the actuator board 71 and compress the connecting element 73, and then the actuator switch 72 disconnects the external circuit 90 to avoid the bag 30 to be over expanded.

Figure 21:
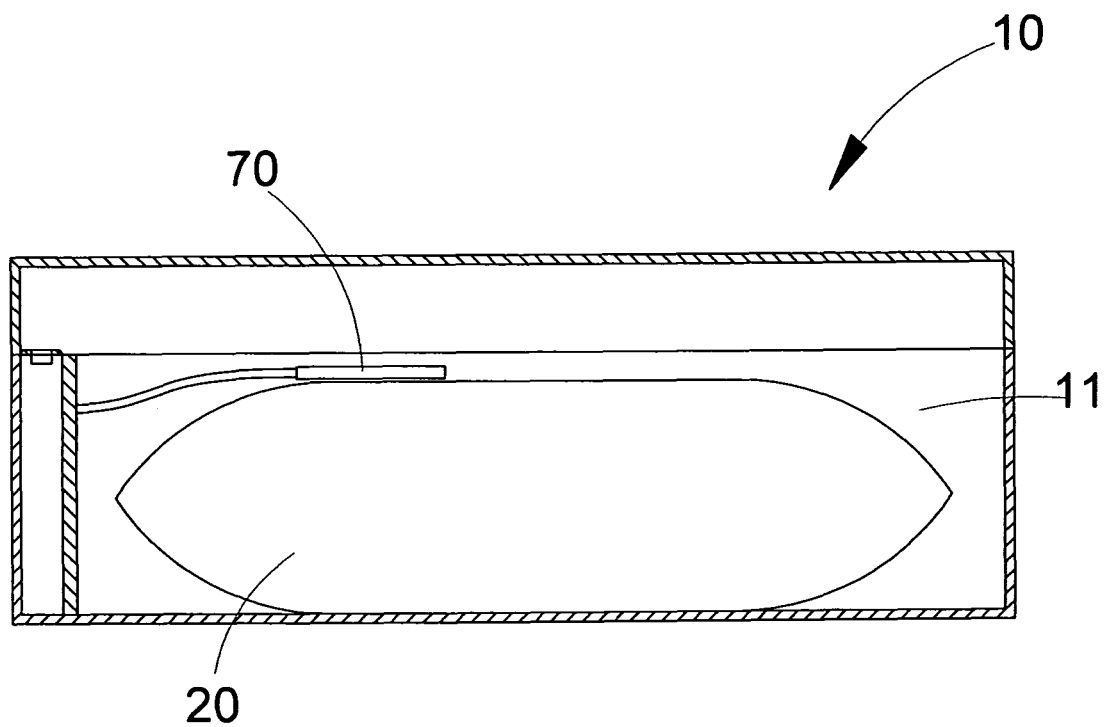
FIG. 21 is a schematic view of a protection device with a rechargeable warmer bag therein according to the above preferred embodiment of the present invention.

As shown in FIG. 21, the monitoring device 60 positioned in the cavity 11 of the protection device 10 comprises an actuator 70, an alerting device 80, and an external circuit 90, wherein the actuator 70 is connected with the external circuit 90, and is positioned in the cavity 11 of the protection device.

The actuator 70 can be embodied as a temperature measuring meter. When the rechargeable warmer bag 20 is being charged in the cavity 11 of the protection device, the rechargeable warmer bag 20 is monitored by the monitoring device 60. The actuator 70 has a plurality of preset value for cutting off the power. When the rechargeable warmer bag 20 is heated to be over expanded, and the temperature of the rechargeable warmer bag 20 is up to the preset value, the actuator 70 disconnects the external circuit 90 to protect the rechargeable warmer bag 20 for explosion.

The altering device 80, which is connected with the actuator 70 and the external circuit 90, comprises a visional altering device 81 and an audio alerting device 82. When the rechargeable warmer bag 20 is charged in the cavity 11 of the protection device, the rechargeable warmer bag 20 is monitored by the monitoring device 60. When the rechargeable warmer bag 20 is heated to be over expanded, the actuator 70 disconnects the external circuit 90. At the same time, the actuator 70 conducts the visional alerting device 81 and the audio alerting device 82 with the external circuit 90, so the visional alerting device 81 is illuminating and the audio alerting device 82 produces sound to alert the user.

Figure 22:
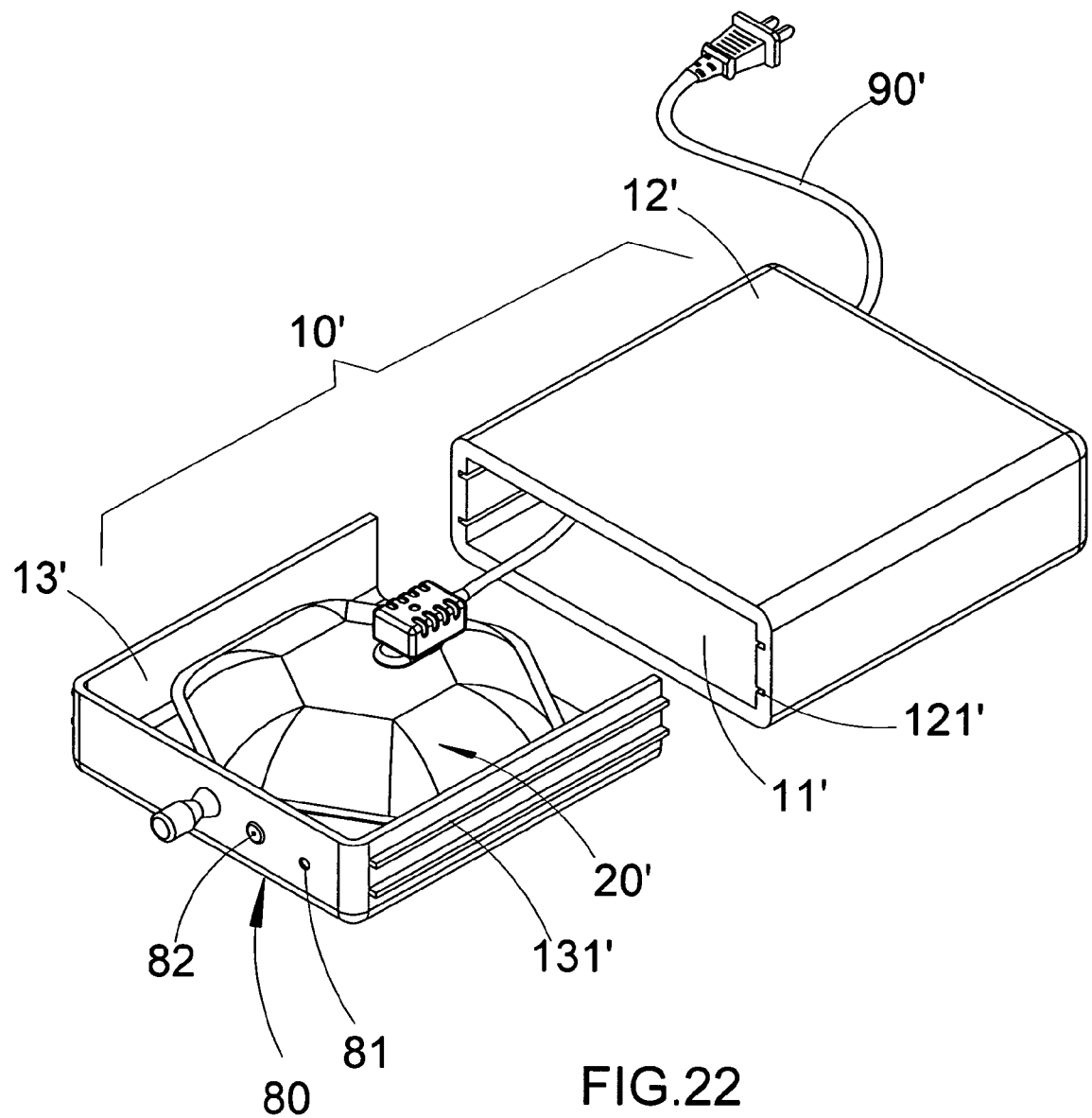
FIG. 22 is a perspective view of an alternative mode of the charge warmer device according to the above preferred embodiment of the present invention.
Figure 23:
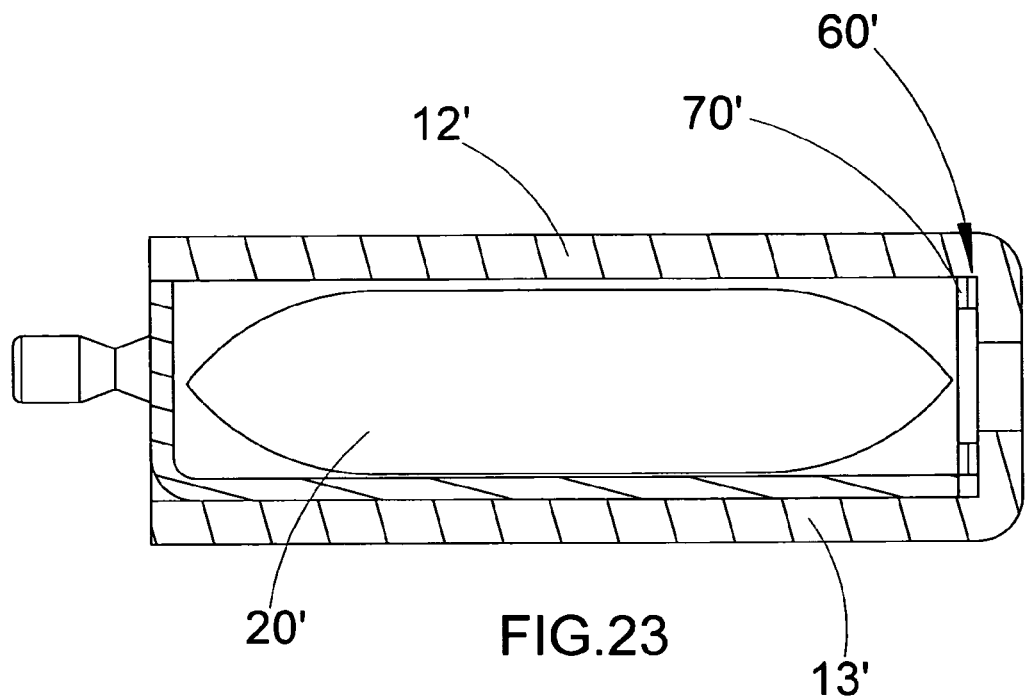
FIG. 23 is a schematic view of an alternative mode of a protection device with a rechargeable warmer bag therein according to the above preferred embodiment of the present invention.
Figure 24:
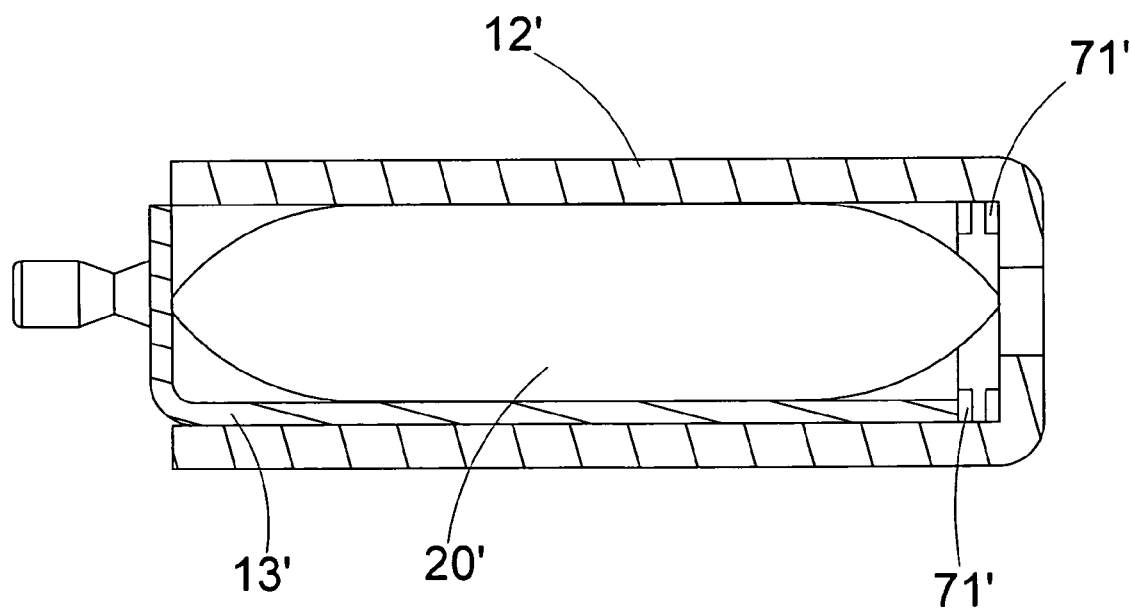
FIG. 24 is a schematic view of an alternative mode of a protection device with an expanded rechargeable warmer bag therein according to the above preferred embodiment of the present invention.

As shown in FIG. 22 to FIG. 24, another alternative mode of the present invention is illustrated.

The warmer device as shown in FIG. 22 comprises a protection device 10' having a protection cavity 11' isolated from outside environment and a rechargeable warmer bag 20' arranged to be charged in the protection device 10'.

The rechargeable warmer bag 20' is disposed in the cavity 11' of the protection device 10' during charging and removed out of the protection device 10' when the rechargeable warmer bag 20' during operation.

The rechargeable warmer bag 20' further comprises:
a bag 30', having a outer surface 31' and a inner surface 32' defining a sealed cavity 33' receiving a predetermined amount of liquid 34' therein;
a heating unit 40' which is disposed in the liquid 34' in the sealed cavity 33' of the bag 30' comprising a plurality of heaters 41';
a charging unit 50', which is connected with the heating unit 40' and disposed between the bag 30' and the heating unit 40', comprising a charging connector 51' and a connecting wire;
a monitoring device 60' arranged in the protection device 10' with respect to the rechargeable warmer bag 20' so as to monitor the rechargeable warmer bag 20' and cut off the power supply of the charging unit 50' of the rechargeable warmer bag 20' when the rechargeable warmer bag 20' is being over-expanded, when the rechargeable warmer bag 20' is in use, the rechargeable warmer bag 20' and the monitoring device 60' are separated.

The protection device 10' further comprises a container 12' and a moving unit 13' which is flexibly mounted in the container 12' and can be moved relative to the container 12'. When the rechargeable warmer bag 20' is being charged, it is positioned in the cavity 11' of the protection device 10' and in the moving unit 13'. When the rechargeable warmer bag 20' is fully charged, the moving unit 13' moves relative to the container 12', so that the rechargeable warmer bag 20' can be taken out of the protection device 10'.

As mentioned above, the container 12' comprises a plurality of slides 121', and the moving unit 13' comprises a plurality of slide rails 131' sliding to-and-fro on the slides 121' of the container 12'.

The monitoring device 60' which is disposed positioned in the cavity 11' of the protection device 10', is positioned between the container 12' and the moving unit 13'. It comprises an actuator 70', an alerting device 80', and an external circuit 90'.

The actuator 70' is connected with the external circuit 90' and positioned between container 12' and the moving unit 13'.

When the rechargeable warmer bag 20' is being charged in the cavity 11 of the protection device 10, the rechargeable warmer bag 20 is monitored by the monitoring device 60. When the rechargeable warmer bag 20' is charged to be heated, the heating bag 20' expands to compress the container to move the moving unit 12' relative to the container 12', and then the actuator 70' between the container 12' and the moving unit 13' switches off the external circuit to cut off the power supply to protect the rechargeable warmer bag 20' from being broken or explosion.

Furthermore, the actuator 70' comprises a first contact unit 71' positioned in the container 12' and a second contact unit 72' positioned on the moving unit 13'.

The altering device 80', which is connected with the actuator 70' and the external circuit 90', comprises a visional altering device 81' and an audio alerting device 82'. When the rechargeable warmer bag 20' is being charged in the cavity 11' of the protection device, the rechargeable warmer bag 20' is monitored by the monitoring device 60'. When the rechargeable warmer bag 20' is heated to be over expanded, the actuator 70' disconnects the external circuit 90'. At the same time, the actuator 70' conducts the visional alerting device 81' and the audio alerting device 82' with the external circuit 90', so that the visional alerting device 81' is illuminating and the audio alerting device 82' produces sound to alert the user.

Figure 25:
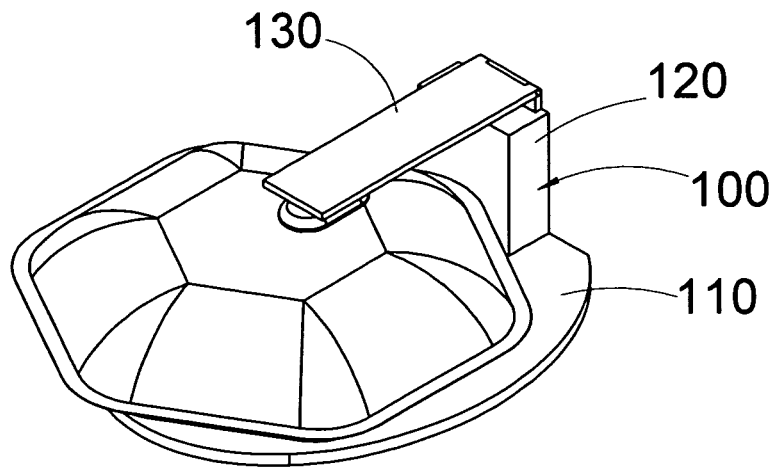
FIG. 25 is a schematic view of a first alternative mode of a protection device with a rechargeable warmer bag therein according to the above preferred embodiment of the present invention.
Figure 26:
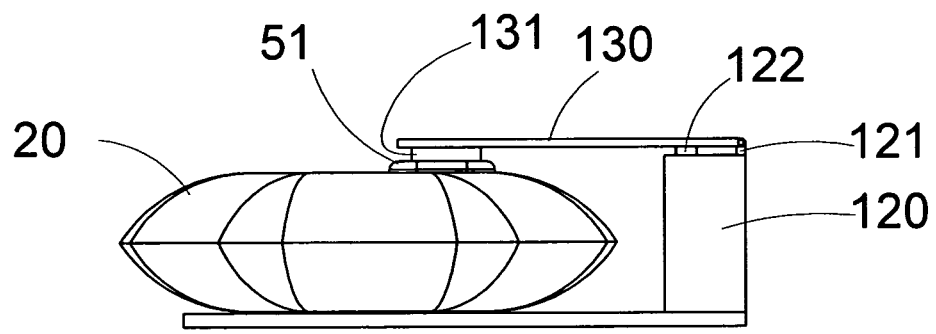
FIG. 26 is a schematic view of a second alternative mode of a protection device with a rechargeable warmer bag therein according to the above preferred embodiment of the present invention.
Figure 27:
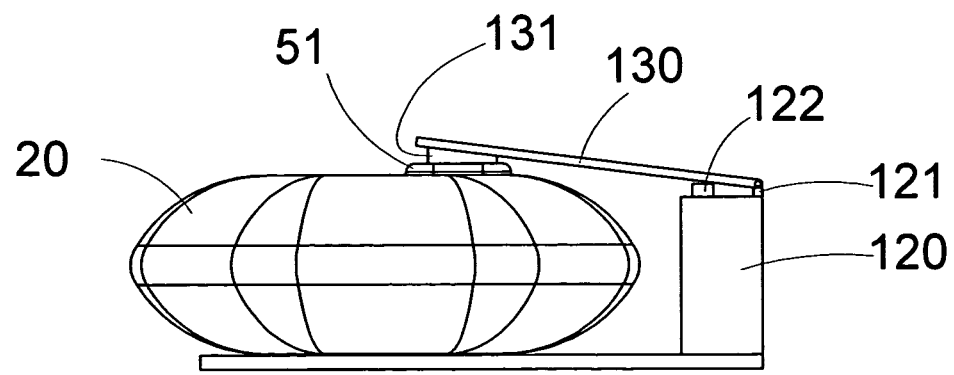
FIG. 27 is a schematic view of a second alternative mode of a protection device with an expanded rechargeable warmer bag therein according to the above preferred embodiment of the present invention.

As shown in FIG. 25 to FIG. 27, another alternative mode of the present invention is illustrated.

The protection device 100 comprises a bottom board 110, a column 120 mounted on the bottom board 110, and a connecting pole 130 connecting to the power. The column 120 comprises a connecting element 121 and an actuator switch 122 mounted on the upper side of the column 120.

The connecting pole 130 is pivotally connected on top of the column and one end of the connecting pole 130 is connected with the connecting element 121 of the column 120. When the rechargeable warmer bag 20 is being charged, the rechargeable warmer bag is positioned in the protection device 10. The other end of the connecting pole 130 is connected with the charging connector 51. The connecting pole 130 further comprises a power plug 131.

When the rechargeable warmer bag 20 is being charged, the rechargeable warmer bag 20 is disposed in the cavity 11 of the protection device 10. The power plug 131 connects to the charging connector 51 of the rechargeable warmer bag 20. At the same time, the connecting pole 130 is pushed down to turn on the actuator switch 122, and then the rechargeable warmer bag is being charged. When the rechargeable warmer bag 20 is over charged to be over-expanded, the rechargeable warmer bag 20 raises it top surface due to the expansion and presses the connecting pole 130 to move upwardly. Then, the connecting pole 130 does not press the actuator switch 122 but releasing the actuator switch 122 to cut off the power supply of the rechargeable warmer bag 20 to protect the rechargeable warmer bag from expansion.

The operating method of the warmer device of the present invention comprises the following steps.

First, open the protection device 10 having the interior protection cavity 11 isolated from outside environment.

Figure 9:
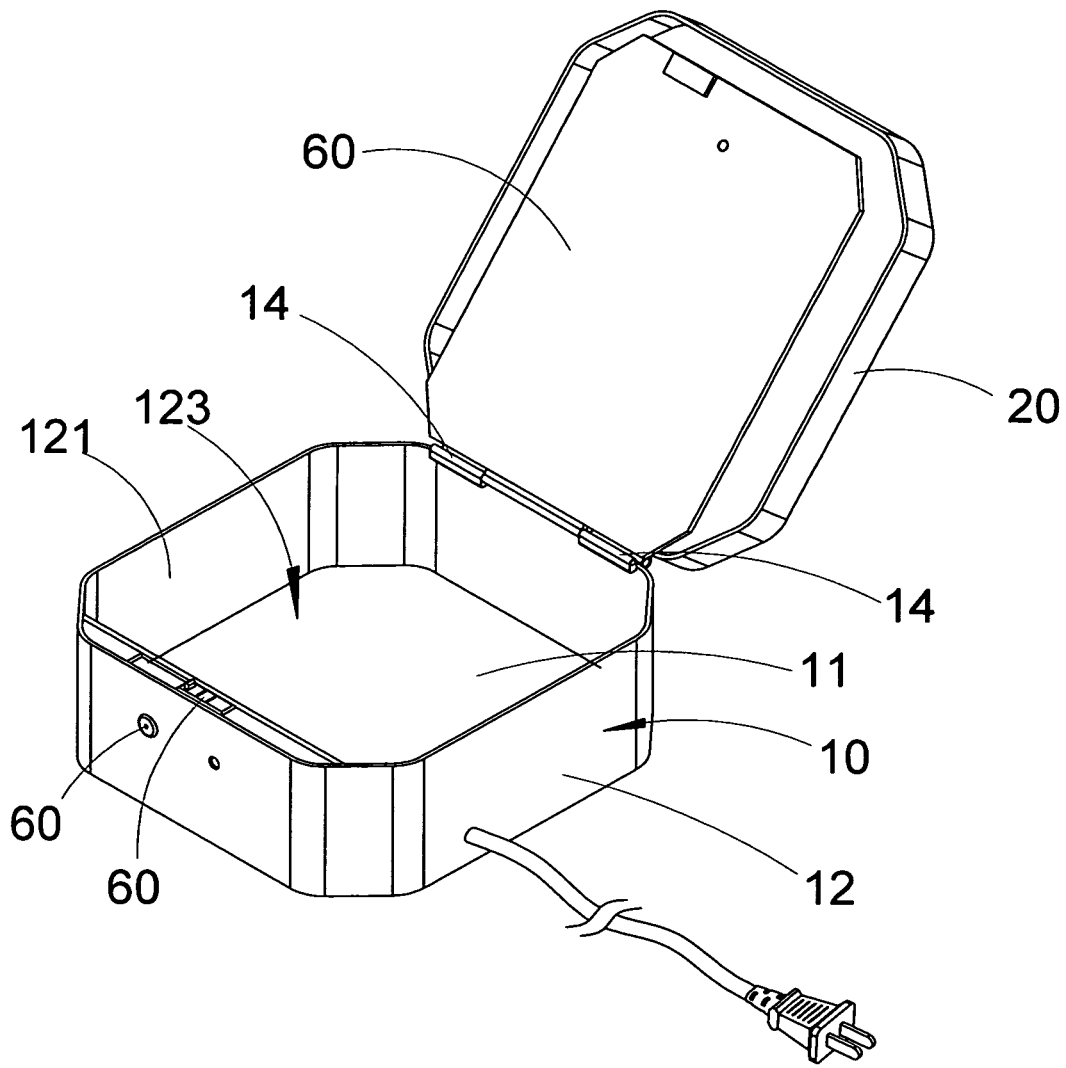
FIG. 9 is a perspective view of a protection device according to the above preferred embodiment of the present invention.
Figure 10:
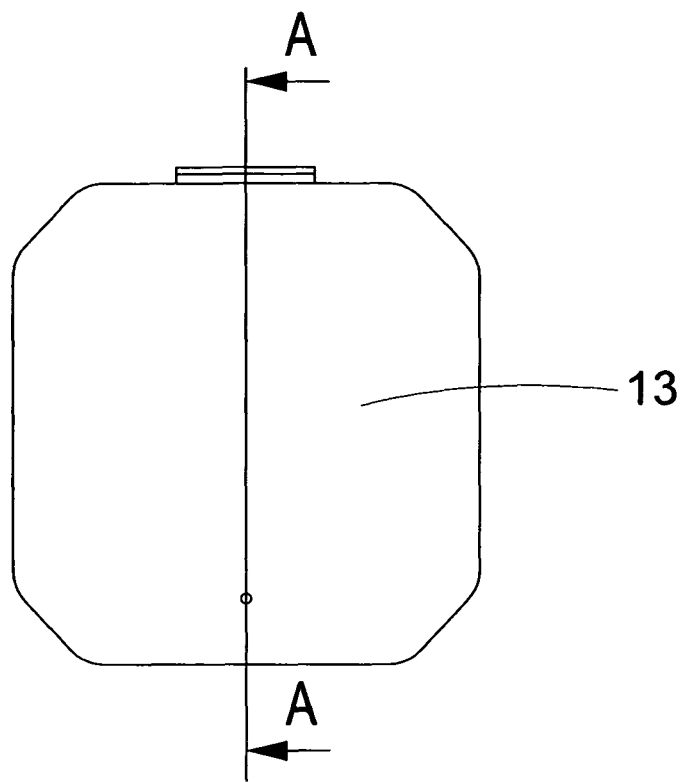
FIG. 10 is a top exterior view of the protection device according to the above preferred embodiment of the present invention.
Figure 11:
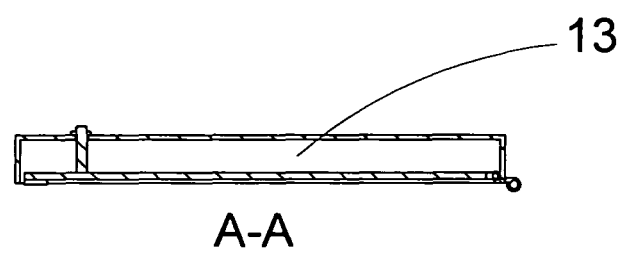
FIG. 11 is an A-A sectional view of a cover of the protection device according to the above preferred embodiment of the present invention.
Figure 12:
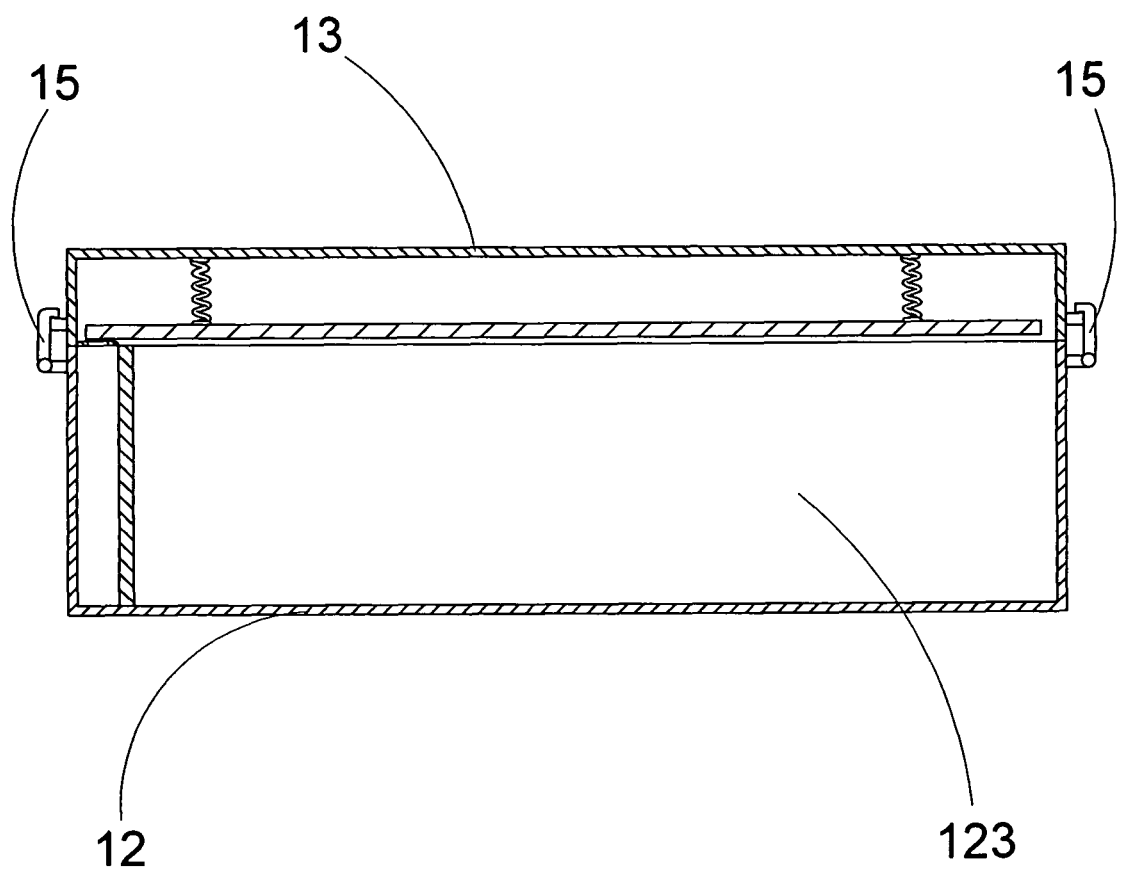
FIG. 12 is a sectional view of the protection device according to the above preferred embodiment of the present invention.

In which, as shown in FIG. 9, the protection device 10 comprises the box 12 and the box cover 13 covering the box 12, wherein the box 12 has the outer surface 122 and the inner surface 121 defining a cavity 123 separated from the outer space by the box cover 13.

Furthermore, as shown in FIG. 22, the protection device 10' further comprises the container 12' and the moving unit 13', wherein the moving unit 13' is flexibly mounted in the container 12', and can move relative to the container 12'. When the rechargeable warmer bag 20' is being charged, it is positioned in the cavity 11' of the protection device 10' and in the moving unit 13'. When the rechargeable warmer bag 20' is fully charged, the moving unit 13' moves with respect to the container 12', so that the rechargeable warmer bag 20' can be taken out of the protection device 10'.

As mentioned above, the container 12' comprises the plurality of slides 121', and the moving unit 13' comprises the plurality of slide rails 131' sliding to-and-fro on to the slides 121' of the container 12'.

Second, put the rechargeable warmer bag 20 into the protection device 10 so as to charge the rechargeable warmer bag 20.

In which, as shown in FIG. 5 to FIG. 8, the rechargeable warmer bag 20 further comprises:

the bag 30, having the outer surface 31 and the inner surface 32 defining the sealed cavity 33 receiving the predetermined amount of liquid 34 therein;

the heating unit 40 which is disposed in the liquid 34 in the sealed cavity 33 of the bag 30 comprising the plurality of heaters 41; and the charging unit 50, which is connected with the heating unit 40 and placed between the bag 30 and the heating unit 40, comprising the charging connector 51 and the connecting wire.

Furthermore, the heating unit 40 positioned in the bag 30 further comprises the connecting tube 42 and the temperature control device 43.

The temperature control device 43, which is connected between the heaters of the heating unit 40, comprises the plurality of temperature controllers 44 with different rated temperature for cutting off the power supply. When the rechargeable warmer bag 20 is being charged, the temperature control device 43 can monitor the temperature of the liquid 34 in the bag 30 in real-time. When the temperature is up to the rated temperature of any temperature controller 44, the temperature control device will cut off the power supply of the charging unit 50.

Furthermore, the connecting tube 42 is fixedly connected between the heaters 41 and the charging connector 51 of the charging unit 50 and supports the plurality of heaters 41 so as to position the heaters 41 within the sealed cavity 33 of the bag 30. When the rechargeable warmer bag 20 is being charged, the connecting tube 42 supports the heaters to ensure the heaters being disposed the sealed cavity 33 of the bag 30 and surrounded by the liquid 34 in the cavity 33.

As the heater 41 of the heating unit 40 converts the electricity to the heat, and conducts the heat to the liquid 34 in the bag 30, the temperature of the liquid 34 is raised and the volume of the liquid 34 is expanded. At this moment, the gas in the bag 30 is expanded too. According to the proportional relation of the gas expansion and liquid expansion when heated, the gas expansion velocity is faster than liquid expansion velocity, so the gas in the cavity squeezes liquid 34 in the cavity. Gradually, the heater 41 of the heating unit 40 separates from the liquid 34, as the liquid level falls due to the rising of the liquid temperature, and then the charge warmer device 20 is cut off from the power supply.

Third, put the rechargeable warmer bag 20 into the protection device 10, so as to charge the rechargeable warmer bag 20. Meanwhile, the rechargeable warmer bag 20 is monitored by a monitoring device 60. When the rechargeable warmer bag 20 is heated to overly expand, the monitoring device 60 cuts the power supply off from the charging unit 50 of the rechargeable warmer bag 20.

In which, as shown in FIG. 14 to FIG. 21, the monitoring device 60 comprises the actuator 70, the altering device 80, and the external circuit 90.

The actuator 70 is connected to the external circuit 90 and is placed in the cavity 11. When the rechargeable warmer bag 20 is being charged in the cavity 11 of the protection device 10, the rechargeable warmer bag 20 is monitored by the monitoring device 60. If the rechargeable warmer bag 20 is heated to be over expanded to touch the actuator 70, the actuator 70 cuts off the power supply from the external circuit 90 so as to protect the rechargeable warmer bag 20 from being broken and explosion.

The actuator 70 comprises the actuator board 71, the actuator switch 72, and the connecting element 73, wherein the actuator board 71 is disposed in the cavity 11 of the protection device 10 and positioned above the rechargeable warmer bag 20 when being charged in the cavity 11 of the protection device.

Furthermore, the actuator board 71 is placed in the box cover 13 of the protection device 10.

One end of the actuator board 71 is pivotally connected to the top of the protection device 10.

And the actuator switch 72 and the connecting element 73 are provided on the other end of the actuator board 71, and the actuator switch 72 is connected to the external circuit 90.

The connecting element 73 can be embodied as an elastic element, such as the spring, which is connected to the box cover 13 of the protection device 10. When the rechargeable warmer bag 20 is over expanded for being charged in the protection device 10, the bag 30 is expanded upward to touch the actuator board 71 and the connecting element 73 on the other end of the actuator board 71 is compressed. And then the actuator switch 72 disconnects the external circuit 90 so as to stop charging the rechargeable warmer bag 20 to avoid the over expansion of the bag 30.

Alternatively, the connecting element 73 can be embodied a hard connecting pole, comprising the fixed pole 731 and the retaining sheet 732. The box cover 13 of the protection device 10 has the through hole 131 therein for receiving the fixed pole 731. The retaining sheet 732 is positioned on top of the fixed pole 731, bigger than the through hole 131 in size.

As mentioned above, the connecting element 73 comprises the plurality of elastic elements. One end of them connects to the top of the protection device 10, and the other end of them connects to the actuator board 71. When the rechargeable warmer bag 20 is being charged in the cavity 11 of the protection device 10, the actuator board 71 is positioned on the upper side of the protection device 10 in relative to the rechargeable warmer bag 20.

The actuator switch 72 is positioned on the actuator board 71 and connects to the external circuit 90.

Furthermore, the elastic element is embodied as the spring.

The actuator 70 comprises the actuator board 71, the actuator switch 72, and the connecting element 73, wherein the actuator board 71 is placed in the cavity 11 of the protection device 10. When the rechargeable warmer bag 20 is being charged in the cavity 11 of the protection device 10, the actuator 71 is positioned surrounding the rechargeable warmer bag 20 and the actuator switch 72 is positioned between the actuator board 71 and the external circuit 90.

The connecting element 73 is connected with the side wall of the protection device. If rechargeable warmer bag 20 is heated to be over expanded as charged in the protection device 10, the bag 30 expands to touch the actuator board 71 and compress the connecting element 73, and then the actuator switch 72 disconnects the external circuit 90 to avoid the bag 30 to be over expanded.

As mentioned above, the actuator 70 can be embodied as the temperature measuring meter. When the rechargeable warmer bag 20 is being charged in the cavity 11 of the protection device, the rechargeable warmer bag 20 is monitored by the monitoring device 60. The actuator 70 has the plurality of preset value for cutting off the power. When the rechargeable warmer bag 20 is heated to be over expanded, and the temperature of the rechargeable warmer bag 20 is up to the preset value, the actuator 70 disconnects the external circuit 90 to protect the rechargeable warmer bag 20 for being broken and explosion.

Furthermore, as shown in FIG. 22 to FIG. 24, the monitoring device 60', which is disposed in the cavity 11' of the protection device 10' and positioned between the container 12' and the moving unit 13', comprises the actuator 70', the alerting device 80', and the external circuit 90'.

The actuator 70' is connected with the external circuit 90' and positioned between container 12' and the moving unit 13'.

When the rechargeable warmer bag 20' is being charged in the cavity 11 of the protection device 10, the rechargeable warmer bag 20 is monitored by the monitoring device 60. When the rechargeable warmer bag 20' is charged to be heated, the heating bag 20' expands to compress the container to move the moving unit 12' with respect to the container 12', and then the actuator 70' between the container 12' and the moving unit 13' switches off the external circuit 90' to cut off the power supply to protect the rechargeable warmer bag 20' from being broken and explosion.

Furthermore the actuator 70' comprises the first contact unit 71' positioned in the container 12' and the second contact unit 72' positioned on the moving unit 13'.

The altering device 80', which is connected with the actuator 70' and the external circuit 90', comprises the visional altering device 81' and the audio alerting device 82'. When the rechargeable warmer bag 20' is being charged in the cavity 11' of the protection device, the rechargeable warmer bag 20' is monitored by the monitoring device 60'. When the rechargeable warmer bag 20' is heated to be over expanded, the actuator 70' disconnects the external circuit 90'. At the same time, the actuator 70' conducts the visional alerting device 81' and the audio alerting device 82' with the external circuit 90', so the visional alerting device 81' is illuminating and the audio alerting device 82' produces sound to alert the user.

Fourth, when the rechargeable warmer bag 20 is fully charged in the protection device 10, take the rechargeable warmer bag 20 out of the protection device, so as to detach the rechargeable warmer bag from the protection device 10.

Figure 28:
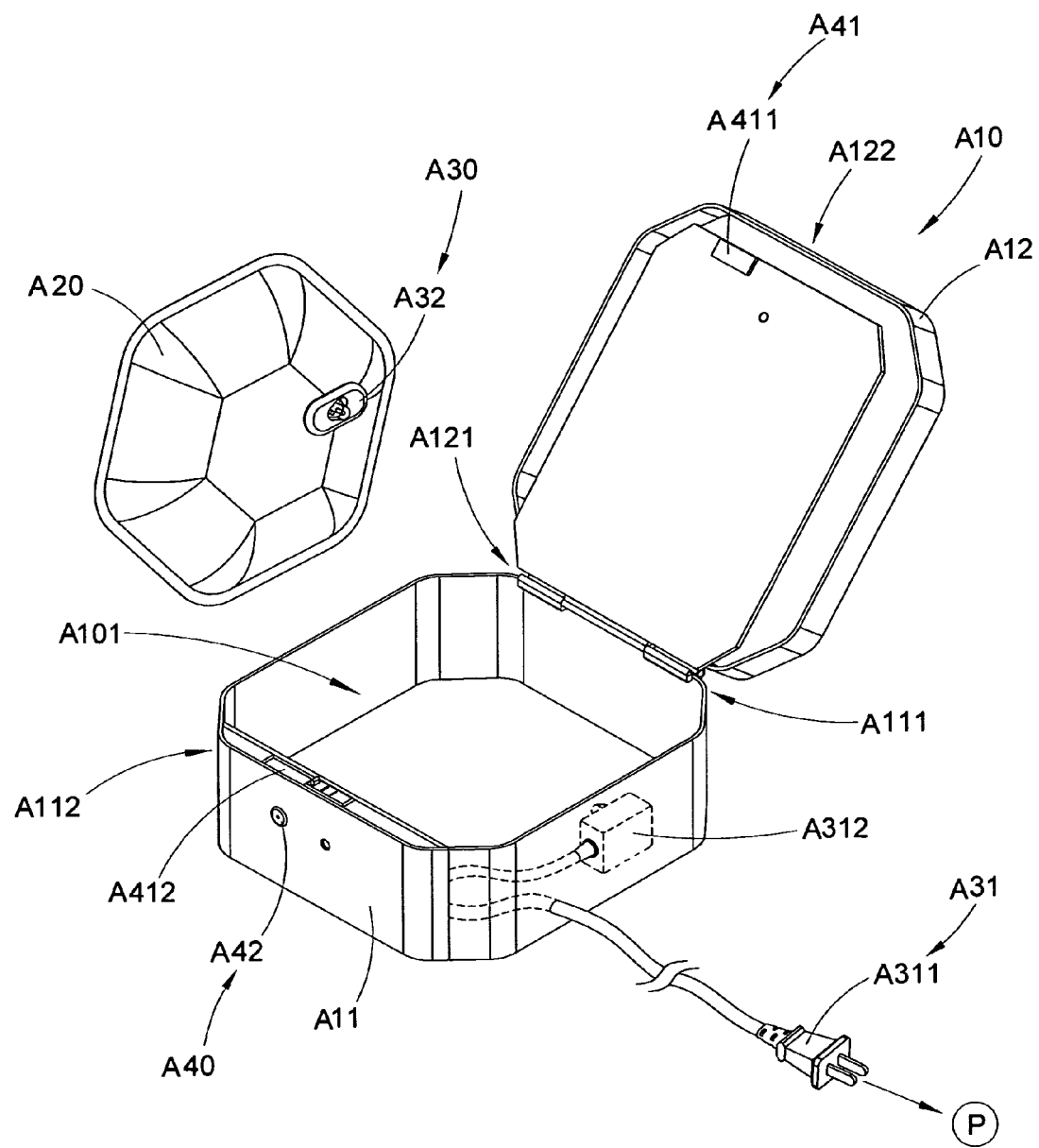
FIG. 28 is a perspective view of a portable warmer according to a preferred embodiment of the present invention.
Figure 31:
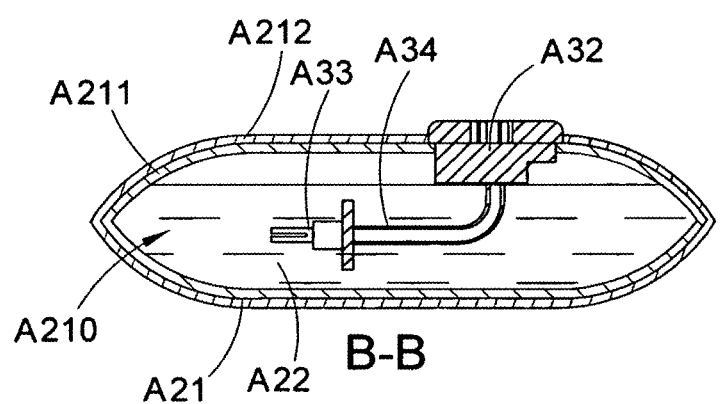
FIG. 31 is a sectional view of the warmer bag according to the above preferred embodiment of the present invention, illustrating the position of the heating element.

Referring to FIGS. 28 and 31 of the drawings, a portable warmer according to a preferred embodiment of the present invention is illustrated, wherein the portable warmer comprises a casing A10 having a receiving compartment A101, and a warmer bag A20 comprising a bag body A21 defining a fluid cavity A210 therein and a heat exchanging fluid A22 sealed and contained in the fluid cavity A210 of the bag body A20. According to the preferred embodiment, the heat exchanging fluid A22 is saline water containing approximately 1% salt dissolving in water by weight.

The portable warmer further comprises a heating arrangement A30 and a safety arrangement A40.

The heating arrangement A30 comprises a power cable A31, an electric terminal A32 provided at the bag body A21, and a heating element A33. The power cable A31 has a power outlet A311 extended out of the casing A10 for electrically connecting with an external power source P and a power adapter A312 extended into the receiving compartment A101.

The heating element A33 is supported in the fluid cavity A210 and is electrically coupled with the electric terminal A32, wherein when the warmer bag A20 is disposed in the receiving compartment A101, the power adapter A312 of the power cable A31 is detachably and electrically coupled with the electric terminal A32 for electrically connecting the heating element A33 with the external power source P so as to heat up the heat exchanging fluid A22 at a predetermined usable temperature.

The safety arrangement A40 is electrically coupling with the heating arrangement A30, wherein when the heat exchanging fluid A22 is heated above the usable temperature, the safety arrangement A40 automatically cuts off an electrical connection between the heating element A33 and the external power source P for preventing the heat exchanging fluid A22 from being overheated.

According to the preferred embodiment, the bag body A21 of the warmer bag A20 is made of flexible material that the warmer bag A20 seals and contains the heat exchanging fluid A22 in a stretchable manner. The bag body A21 is constructed by a plurality of layers as shown in FIG. 31, wherein the innermost layer A211 is made of waterproof material to seal the heat exchanging fluid A22 within the fluid cavity A210 while the outermost layer A212 is made of soft material to be touched by the user body.

Accordingly, when the heat exchanging fluid A22 is at the usable temperature, the heat exchanging fluid A22 expands its volume in comparison with the heat exchanging fluid A22 at a normal room temperature. According to the preferred embodiment, the heat exchanging fluid A22 is heated up at approximately 70° C. In addition the bag body A21 will be expanded approximately 1 to 2 cm by size when the heat exchanging fluid A22 is heated up from the normal room temperature to 70° C.

As shown in FIG. 31, the heat exchanging fluid A22 is partially filled in the bag body A21 of the warmer bag A20 that when the warmer bag A20 is disposed in the casing A10, a bottom portion of the warmer bag A20 is filled with the heat exchanging fluid A22 while an upper portion of the warmer bag A20 is filled with gas. In other words, when the warmer bag A20 is laid flat in receiving compartment A101 of the casing A10, the heating element A33 is submerged at the heat exchanging fluid A22. Therefore, when the heat exchanging fluid A22 is heated up, the bag body A21 provides enough room for the volume-expansion of the heat exchanging fluid A22 without popping the bag body A21.

The heating arrangement A30 further comprises a retention arm A34 extended from the electric terminal A32 to the heating element A33 to retain the heating element A33 at a position that the heating element A33 is submerged at the heat exchanging fluid A22 to effectively heat up the heat exchanging fluid A22.

Figure 29:
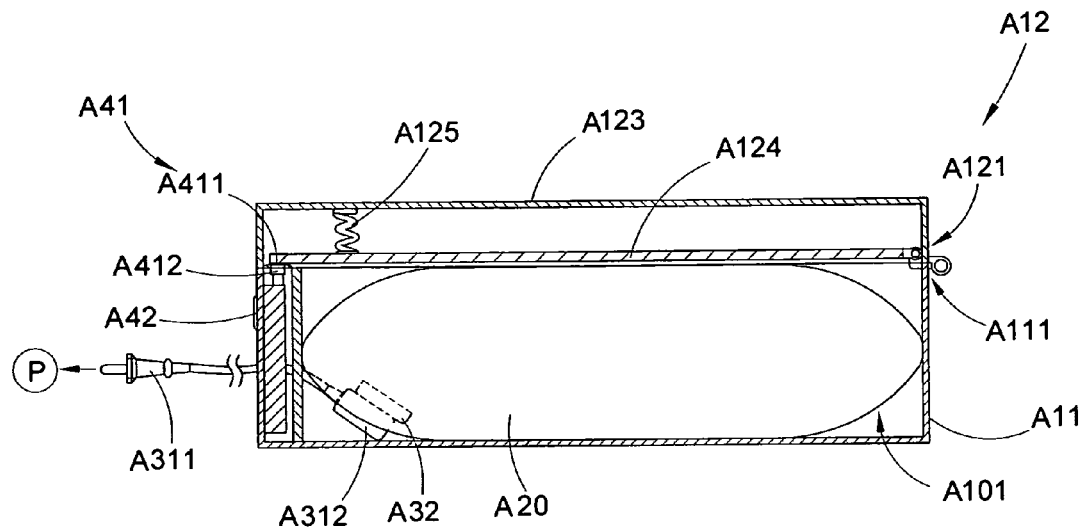
FIG. 29 is a schematic view of the warmer bag disposed in the casing during heating operation according to the above preferred embodiment of the present invention.

As shown in FIG. 29, the safety arrangement A40 comprises a contact switch A41 provided at the casing A10 to cut off the electrical connection between the heating element A33 and the external power source P when the heat exchanging fluid A22 is heated at the usable temperature. The contact switch A41 is electrically coupled with the power cable A31 between the power outlet A311 and the power adapter A312 such that the contact switch A41 cuts off the electrical connection between the power outlet A311 and the power adapter A312.

According to the preferred embodiment, the casing A10 comprises a base housing A11 and a cover housing A12 pivotally coupling with the base housing A11 to enclose the receiving compartment A101. The base housing A11 has a first housing edge A111 and an opposed second housing edge A112. The cover housing A12 has a pivot edge 121 pivotally coupling with the first housing edge A111 of the base housing A11 and a folding edge 122 folded to align with the second housing edge A112 of the base housing A11.

Accordingly, the contact switch A41 comprises a first contacting terminal A411 provided at the second housing edge A112 of the base housing A11 and a second contacting terminal A412 provided at the folding edge A122 of the cover housing A12 to align with the first contacting terminal A411. Therefore, when the cover housing A12 is pivotally folded on the base housing A11, the second contacting terminal A412 contacts with the first contacting terminal A411 so as to close the electrical connection between the power outlet 311 and the power adapter A312.

Figure 30:
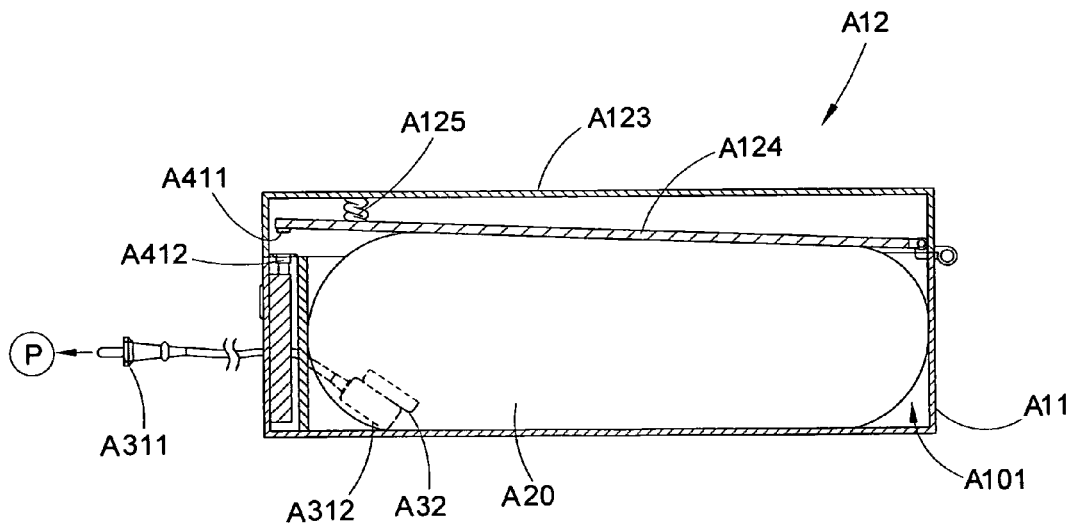
FIG. 30 is a schematic view of the warmer bag disposed in the casing during cut off operation according to the above preferred embodiment of the present invention.

When the heat exchanging fluid A22 is at the normal room temperature, the cover housing A12 is pivotally folded to contact the second contacting terminal A412 with the first contacting terminal A411 to close the electrical connection between the heating element A33 and the external power source P, as shown in FIG. 29. When the heat exchanging fluid A22 is at the usable temperature, the warmer bag A20 is expanded to move the second contacting terminal A412 away from the first contacting terminal A411 so as to cut off the electrical connection between the heating element A33 and the external power source P, as shown in FIG. 30. In other words, when the heat exchanging fluid A22 is at the normal room temperature, the cover housing A12 can be fully covered on top of the base housing A11 to conceal the receiving compartment A101. Once the heat exchanging fluid A22 is heated up at the usable temperature, the warmer bag A20 is expanded with a predetermined volume enough to push the second contacting terminal A412 away from the first contacting terminal A411. It is worth to mention that when the warmer bag A20 is disposed in the casing A10, the two sides of the warmer bag A20 are biased against two inner sidewalls of the casing A10 respectively. Therefore, the warmer bag A20 will be expanded at its transverse direction.

As shown in FIGS. 29 and 30, the cover housing A12 comprises an outer shelter A123 pivotally folded on the base housing A11 to enclose the receiving compartment A101, and an inner pivot cover A124 pivotally coupling with the outer shelter A123, wherein the second contacting terminal A412 is provided at the inner pivot cover A124 such that when the warmer bag A20 is expanded to pivotally and upwardly move the inner pivot cover A124 for moving the second contacting terminal A412 away from the first contacting terminal A411, the outer shelter A123 is remained at its position to enclose the warmer bag A20 in the receiving compartment A101. The inner pivot cover A124 is pivotally coupled with the outer shelter A123 at the pivot edge A121 thereof.

The cover housing A12 further comprises a resilient element A125 supported between the outer shelter A123 and the inner pivot cover A124 for applying an urging force against the inner pivot cover A124 to ensure the second contacting terminal A412 being contacted with the first contacting terminal A411 when the heat exchanging fluid A22 is heated under the unable temperature.

According to the preferred embodiment, the safety arrangement A40 further comprises a signal generator A42 provided at an outer side of the base housing A11 and electrically coupled with the contact switch A41 for generating a notifying signal when the second contacting terminal A412 is moved apart from the first contacting terminal A411. The signal generator A42 comprises a LED light for generating a light signal as the notifying signal and/or a buzzer for generating a sound signal as the notifying signal. Therefore, the signal generator A42 will notify the user the warmer bag A20 is ready to use when the heat exchanging fluid A22 is heated up at the usable temperature. In addition, since the contact switch A41 prevents the heat exchanging fluid A22 from being overheated, the user is able to remove the warmer bag A20 without being burned by the warmer bag A20 once the notifying signal is generated.

Figure 32:
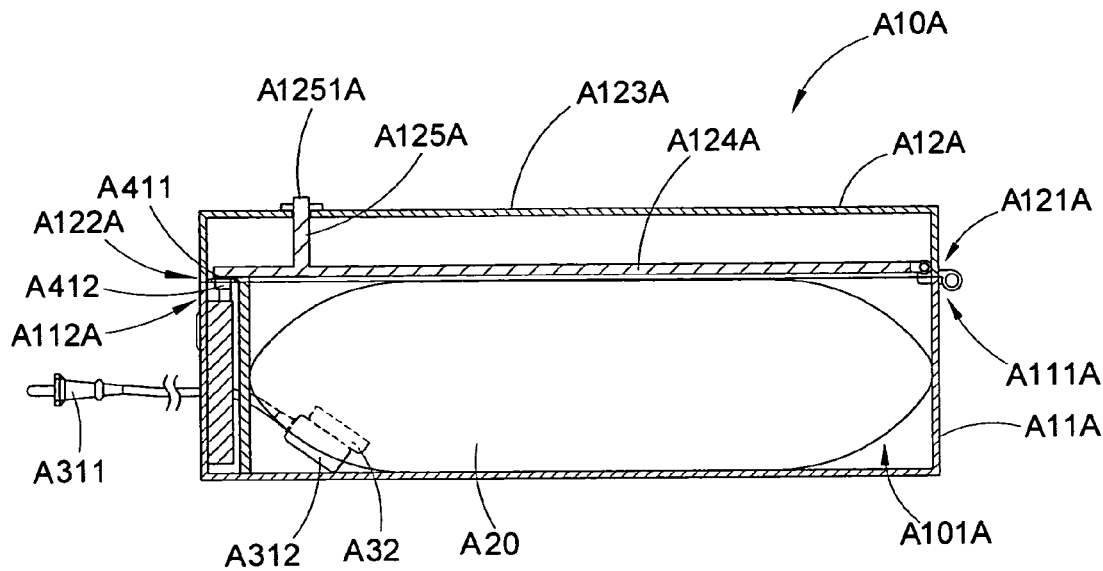
FIG. 32 illustrates a first alternative mode of the casing incorporating with the safety arrangement according to the preferred embodiment of the present invention, illustrating the warmer bag during heating operation

FIG. 32 illustrates a first alternative mode of the casing A10A incorporating with the safety arrangement A40. The casing A10A comprises a base housing A11A and a cover housing A12A pivotally coupling with the base housing 11A to enclose the receiving compartment A101A. The base housing A11A has a first housing edge A111A and an opposed second housing edge A121A. The cover housing A12A has a pivot edge A121A pivotally coupling with the first housing edge A111A of the base housing A11A and a folding edge A122A folded to align with the second housing edge A112A of the base housing A11A. It is worth to mention that when the warmer bag A20 is disposed in the casing A10A, the two sides of the warmer bag A20 are biased against two inner sidewalls of the casing A10A respectively. Therefore, the warmer bag A20 will be expanded at its transverse direction.

The first contacting terminal A411 of the contact switch A41 is provided at the second housing edge A112A of the base housing A11A and a second contacting terminal A412 is provided at the folding edge A122A of the cover housing A12A to align with the first contacting terminal A411.

The cover housing A12A comprises an outer shelter A123A pivotally folded on the base housing A11A to enclose the receiving compartment A101A, and an inner pivot cover A124A pivotally coupling with the outer shelter A123A, wherein the second contacting terminal A412 is provided at the inner pivot cover A124A such that when the warmer bag A20 is expanded to pivotally and upwardly move the inner pivot cover A124A for moving the second contacting terminal A412 away from the first contacting terminal 411, the outer shelter A123A is remained at its position to enclose the warmer bag A20 in the receiving compartment A101A.

The cover housing A12A further comprises an operation shaft A125A having an affixing end affixed to the inner pivot cover A124A and an enlarged head A1251A which is extended through the outer shelter A123A and is arranged in such a manner that when the enlarged head A1251A is sat on the outer shelter A123A, the second contacting terminal A412 is contacted with the first contacting terminal A411, and when the enlarged head A1251A is lifted above the outer shelter A123A, the inner pivot cover A124A is pivotally lifted up to move the second contacting terminal A412 away from the first contacting terminal A411.

Figure 34:
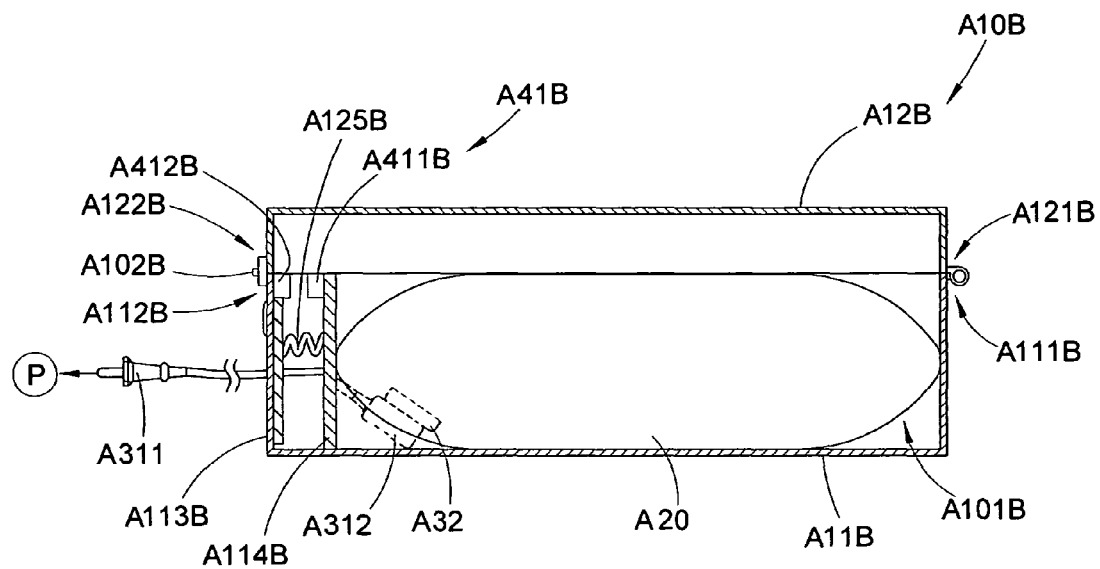
FIG. 34 illustrates a second alternative mode of the casing incorporating with the safety arrangement according to the preferred embodiment of the present invention, illustrating the warmer bag during heating operation.
Figure 35:
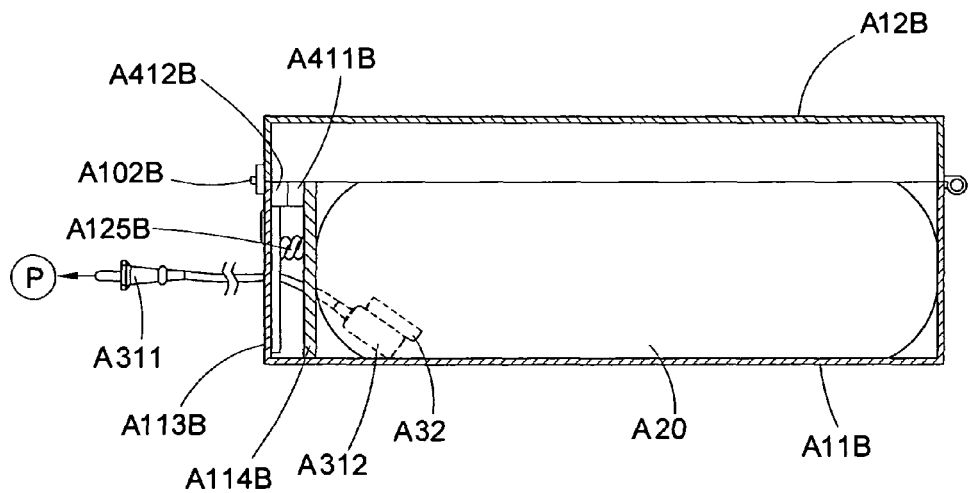
FIG. 35 illustrates the second alternative mode of the casing incorporating with the safety arrangement according to the preferred embodiment of the present invention, illustrating the warmer bag during cut off operation.

FIGS. 34 and 35 illustrate a second alternative mode of the casing A10B incorporating with the safety arrangement A40B. The casing A10B comprises a base housing A11B and a cover housing A12B pivotally coupling with the base housing A11B to enclose the receiving compartment A101B. The base housing A11B has a first housing edge A111B and an opposed second housing edge A121B. The cover housing A12B has a pivot edge A121B pivotally coupling with the first housing edge A111B of the base housing A11B and a folding edge A122B folded to align with the second housing edge A112B of the base housing A11B. A locker A102B is provided to lock up the cover housing A12B with the base housing A11B.

The base housing A11B comprises an outer affixing wall A113B and an inner movable wall A114B slidably supported within the receiving compartment A101, wherein when the heat exchanging fluid A22 is at the normal room temperature, the movable wall A114B is positioned apart from the affixing wall A113B and when the heat exchanging fluid A22 is at the usable temperature, the warmer bag A20 is expanded to move the movable wall A114B towards the affixing wall A113B. It is worth to mention that when the warmer bag A20 is disposed in the casing A10B, the top and bottom sides of the warmer bag A20 are biased against the inner top side and the inner bottom side of the casing A10B respectively. Therefore, the warmer bag A20 will be expanded at its longitudinal direction.

As shown in FIG. 34, the first contacting terminal A411B of the contact switch A41B is provided at the affixing wall A113B of the base housing A11B and the second contacting terminal A412B is provided at the movable wall A114B of the base housing A11B to align with the first contacting terminal A411B. Accordingly, the contact switch A41B keeps the electrical connection between the heating element A33 and the external power source P when the movable wall A114B is positioned apart from the affixing wall A113B to separate the second contacting terminal A412B from the first contacting terminal A411B. When the heat exchanging fluid A22 is at the usable temperature, the warmer bag A20 is expanded to move the movable wall A114B towards the affixing wall A113B to contact the second contacting terminal A412B with the first contacting terminal A411B such that the contact switch A41B cuts off the electrical connection between the heating element A33 and the external power source P. In other words, when the movable wall A114B is positioned apart from the affixing wall A113B, the second contacting terminal A412B is non-contacted with the first contacting terminal A411B to keep the electrical connection between the heating element A33 and the external power source P, and when the movable wall A114B is moved to the affixing wall A113B, the second contacting terminal A412B is contacted with the first contacting terminal A411B to cut off the electrical connection between the heating element A33 and the external power source P.

As shown in FIGS. 34 and 35, the base housing A11B further comprises a resilient element A125B supported between the affixing wall A113B and the movable wall A114B for applying an urging force against the movable wall A114B to ensure the second contacting terminal A412B being non-contacted with the first contacting terminal A411B when the heat exchanging fluid A22 is heated under the normal room temperature.

Figure 36:
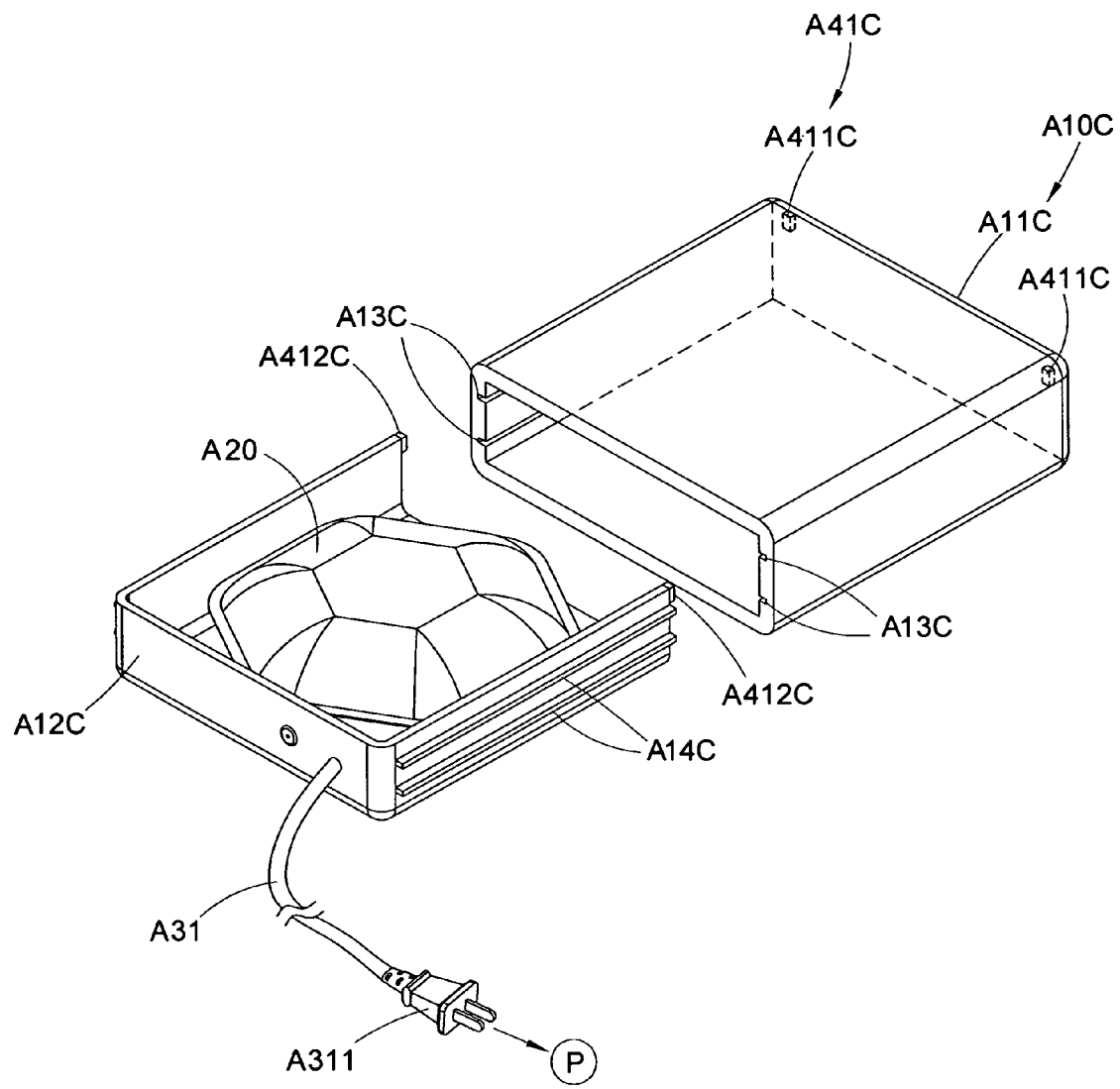
FIG. 36 illustrates a third alternative mode of the casing incorporating with the safety arrangement according to the preferred embodiment of the present invention.

FIG. 36 illustrates a third alternative mode of the casing A10C. The casing A10C comprises a hollow shaped stationary housing A11C having an opening end and an opposed wall end, and a U-shaped cross sectional sliding housing A12C slidably received in the stationary housing A11C for the warmer bag A20 disposing within the stationary housing A11C, wherein the contact switch A41C provided at the casing to cut off the electrical connection between the heating element A33 and the external power source P when the heat exchanging fluid A22 is heated at the usable temperature.

Figure 37:
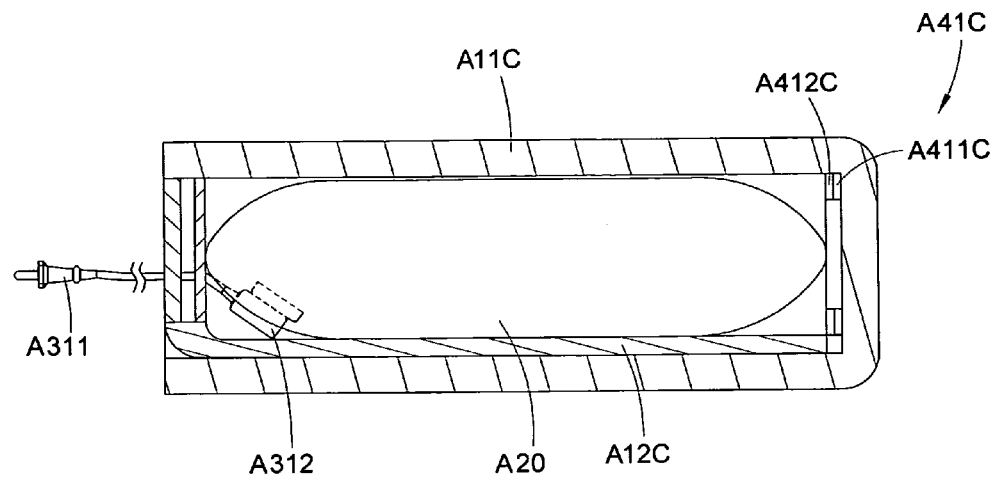
FIG. 37 illustrates the third alternative mode of the casing incorporating with the safety arrangement according to the preferred embodiment of the present invention, illustrating the warmer bag during heating operation.
Figure 38:
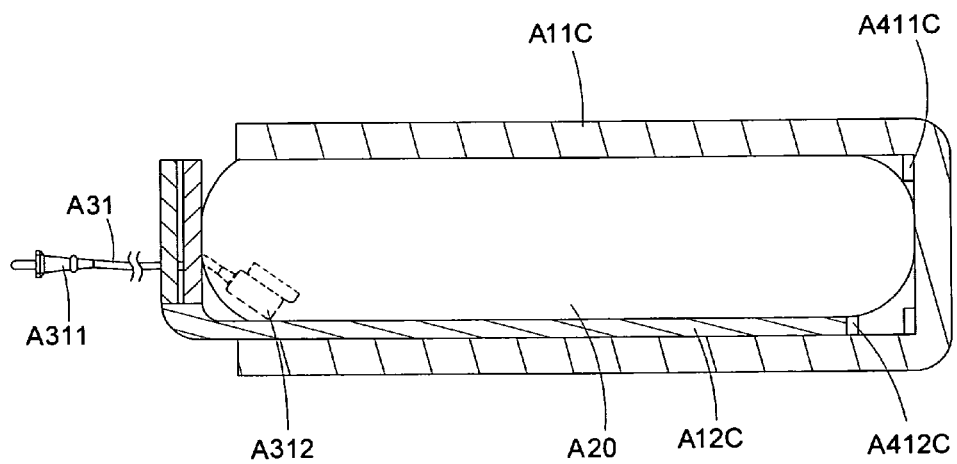
FIG. 38 illustrates the third alternative mode of the casing incorporating with the safety arrangement according to the preferred embodiment of the present invention, illustrating the warmer bag during cut off operation.

Accordingly, the contact switch A41C, which is electrically coupled with the power cable A31 between the power outlet A311 and the power adapter A312, comprises a first contacting terminal A411C provided at the wall end of the stationary housing A11C and a second contacting terminal A412C which is provided at a corresponding edge of the sliding housing A12C to align with the first contacting terminal A411C and is arranged in such a manner that when the heat exchanging fluid A22 is at the normal temperature, the sliding housing A12C is received in the stationary housing A11C to contact the second contacting terminal A412C with the first contacting terminal A411C to close the electrical connection between the heating element A33 and the external power source P, as shown in FIG. 37, and when the heat exchanging fluid A22 is at the usable temperature, the warmer bag A20 is expanded to slidably push the sliding housing A12C to move the second contacting terminal A412C away from the first contacting terminal A411C so as to cut off the electrical connection between the heating element A33 and the external power source P, as shown in FIG. 38.

It is worth to mention that when the warmer bag A20 is disposed in the casing A10C, the top and bottom sides of the warmer bag A20 are biased against the inner top side and the inner bottom side of the casing A10C respectively. Therefore, the warmer bag A20 will be expanded at its longitudinal direction.

In order to guide the contact between the first and second contacting terminals A411C, A412C, the casing A10C further contains two or more sliding tracks A13C provided at two sidewalls of the stationary housing A11C respectively and comprises two or more sliding guiders A14C provided at two sidewalls of the sliding housing A12C to slidably engage with the sliding tracks A13C respectively so as to guide the sliding housing A12C being slid within the stationary housing A11C and to ensure the second contacting terminal A412C being aligned with the first contacting terminal A411C.

Figure 39:
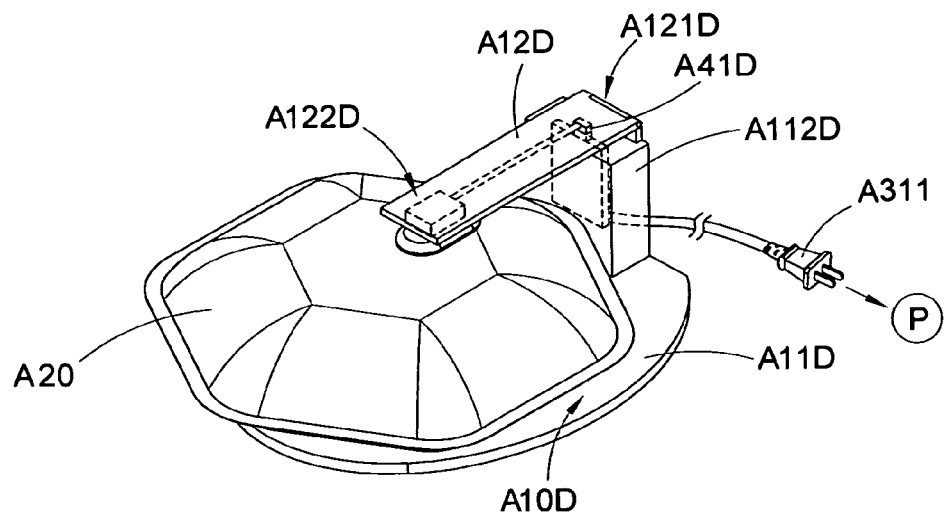
FIG. 39 illustrates a fourth alternative mode of the casing incorporating with the safety arrangement according to the preferred embodiment of the present invention.

FIG. 39 illustrates a fourth alternative mode of the casing A10D in which the warmer bag A20 is not fully concealed in the casing A10D. The casing A10D comprises a base housing A11D and a pivot arm A12D. The base housing A11D comprises a supporting platform A111D for the warmer bag A20 supporting thereon and a supporting shaft A112D upwardly extended from the supporting platform A111D. The pivot arm A12D has a pivot end A121D pivotally coupling at a top end of the supporting shaft A112D and a contacting end A122D sitting on top of the warmer bag A20.

Figure 40:
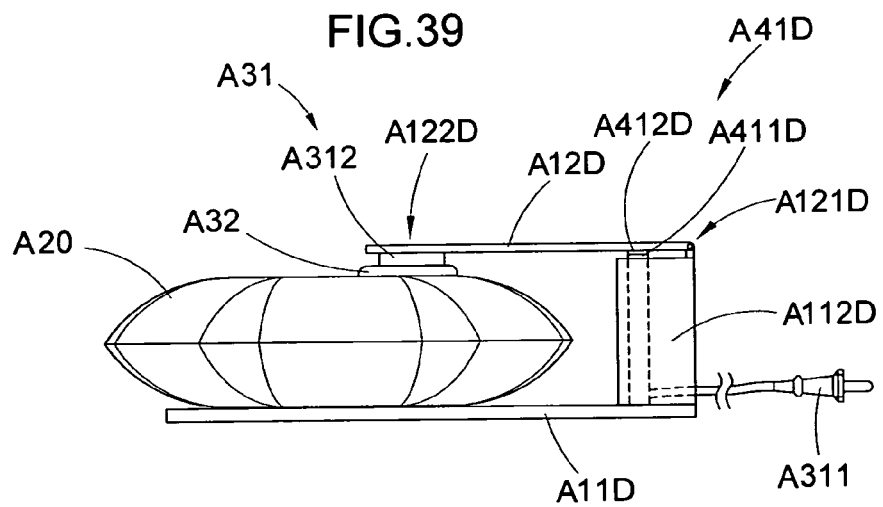
FIG. 40 illustrates the fourth alternative mode of the casing incorporating with the safety arrangement according to the preferred embodiment of the present invention, illustrating the warmer bag during heating operation.
Figure 41:
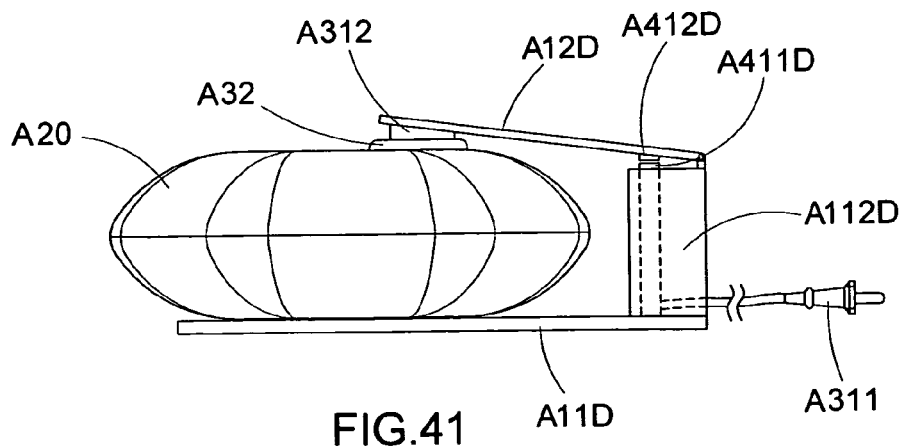
FIG. 41 illustrates the fourth alternative mode of the casing incorporating with the safety arrangement according to the preferred embodiment of the present invention, illustrating the warmer bag during cut off operation.

The contact switch A41D is provided at the casing A10D to cut off the electrical connection between the heating element A33 and the external power source P when the heat exchanging fluid A22 is heated at the usable temperature. Accordingly, the contact switch A41D is electrically coupled with the power cable A31 between the power outlet A311 and the power adapter A312. As shown in FIGS. 39 to 41, the power adapter A312 is provided at the contacting end A122D of the pivot arm A12D to electrically couple with the electric terminal A32 at the warmer bag A20.

The contact switch A41D comprises a first contacting terminal A411D provided at the top end of the supporting shaft A112D and a second contacting terminal A412D which is provided at the pivot arm A12D to align with the first contacting terminal A411D and is arranged in such a manner that when the heat exchanging fluid A22 is at the normal temperature, the second contacting terminal A412D is contacted with the first contacting terminal A411D to close the electrical connection between the heating element A33 and the external power source P, as shown in FIG. 40, and when the heat exchanging fluid A22 is at the usable temperature, the warmer bag A20 is expanded to upwardly lifted the contacting end A122D of the pivot arm A12D for moving the second contacting terminal A412D away from the first contacting terminal A411D so as to cut off the electrical connection between the heating element A33 and the external power source P, as shown in FIG. 41. It is worth to mention that the second contacting terminal A412D is provided at the pivot arm A12D at a position between the pivot end A121D and the contacting end A122D to align with the first contacting terminal A411D.

Figure 33:
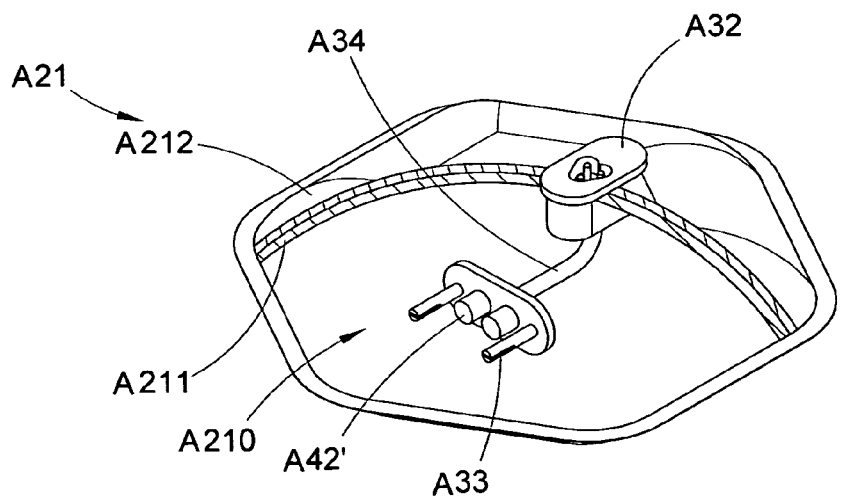
FIG. 33 illustrates an alternative mode of the safety arrangement according to the preferred embodiment of the present invention.

FIG. 33 illustrates an alternative mode of the safety arrangement A40'. The safety arrangement A40' comprises a temperature sensor A42' electrically coupling with the electric terminal A32 at a position within the fluid cavity A210 and arranged to cut off the electrical connection between the heating element A33 and the external power source P when the temperature sensor A42' detects the heat exchanging fluid A22 above the usable temperature.

Accordingly, the retention arm A34 is extended from the electric terminal A32 to the heating element A33 to retain the heating element A33 at a position that the heating element A33 is submerged at the heat exchanging fluid A22 to effectively heat up the heat exchanging fluid A22. The temperature sensor A42' is coupled with the retention arm A34 at a position adjacent to the heating element A33 to detect the temperature of the heat exchanging fluid A22.

It is worth to mention that the temperature sensor A42' can be incorporated with the above mentioned casing A10 and its alternatives to provide dual-safety feature to prevent the heat exchanging fluid A22 from being overheated.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A warmer device, comprising: a rechargeable warmer bag which comprises a bag defining a sealed cavity and receiving a predetermined of liquid therein, and a heating unit supported in said sealed cavity for heating up said liquid, wherein when said liquid is heated up at a usable temperature, said bag is expanded to increase a size thereof; a protection device having an interior protection cavity for disposing said rechargeable warmer bag thereat, a charging device provided at said protection device to operatively connect to said heating unit when said rechargeable warmer bag is disposed at said protection cavity of said protection device; and a monitoring device provided at said protection device to monitor said rechargeable warmer bag, wherein said monitoring device comprises an actuator operatively linked to said charging device and arranged in such a manner that said actuator is switched on to ensure said heating unit being operated to heat up said liquid at said protection cavity before said liquid in said bag is heated up at said usable temperature, wherein said actuator is actuated by said bag when said bag is expanded, such that said actuator is switched off in response to an expansion of said bag at said protection cavity to cut off a power supply of said charging unit for preventing said bag being over-expanded.

2. The warmer device, as recited in claim 1, wherein said protection device comprises an affixing wall and a movable wall, wherein said actuator is provided on at least one of said affixing wall and said movable wall, such that when said bag is expanded, said movable wall is pushed in response to said expansion of said bag to actuate said actuator for cutting off said power supply of said charging unit.

3. The warmer device, as recited in claim 2, wherein said actuator comprises a first contacting terminal provided at said affixing wall and a second contacting terminal provided at said movable wall and arranged in such a manner that when said bag is disposed at said protection cavity that said liquid is heated below said usable temperature, said second contacting terminal is conductively contacted with said first contacting terminal to ensure an operation of said heating unit to heat up said liquid, and when said bag is expanded to push said movable wall, said second contacting terminal is moved apart from said first contacting terminal so as to cut off said power supply of said charging unit.

4. The warmer device, as recited in claim 3, wherein said protection device further comprises a base housing and a pivot cover pivotally coupled with said base housing, wherein said affixing wall and said movable wall are defined at said base housing and said pivot cover respectively, such that when said bag is expanded, said pivot cover is pivotally and upwardly pushed in response to said expansion of said bag to actuate said actuator for cutting off said power supply of said charging unit.

5. The warmer device, as recited in claim 4, wherein said first contacting terminal is provided at said base housing and said second contacting terminal is provided at said pivot cover and arranged in such a manner that when said bag is disposed at said protection cavity that said liquid is heated below said usable temperature, said pivot cover is pivotally and downwardly covered on said bag to conductively contact said second contacting terminal with said first contacting terminal to ensure an operation of said heating unit to heat up said liquid, and when said bag is expanded to pivotally and upwardly push said pivot cover, said second contacting terminal is moved apart from said first contacting terminal so as to cut off said power supply of said charging unit.

6. The warmer device, as recited in claim 5, wherein said protection device further comprises an outer shelter pivotally coupled with said base housing to enclose said pivot cover within said receiving compartment, and a resilient element supported between said outer shelter and said pivot cover for applying an urging force against said pivot cover to ensure said second contacting terminal being contacted with said first contacting terminal before said bag is expanded.

7. The warmer device, as recited in claim 5, wherein said protection device further comprises an outer shelter pivotally coupled with said base housing to enclose said pivot cover within said receiving compartment, and an operation shaft having an affixing end affixed to said pivot cover and an enlarged head which is extended through said outer shelter and is arranged in such a manner that when said enlarged head is sat on said outer shelter, said second contacting terminal is contacted with said first contacting terminal, and when said enlarged head is lifted above said outer shelter, said pivot cover is pivotally lifted up to move said second contacting terminal away from said first contacting terminal.

8. The warmer device, as recited in claim 3, wherein said protection device further comprises a hollow shaped stationary housing having an opening end and an opposed wall end, and a U-shaped cross sectional sliding housing slidably received in said stationary housing for said bag being disposed within said stationary housing, wherein said affixing wall and said movable wall are defined at said stationary housing and said sliding housing respectively, such that when said bag is expanded, said sliding housing is slidably pushed from said stationary housing in response to said expansion of said bag to actuate said actuator for cutting off said power supply of said charging unit.

9. The warmer device, as recited in claim 8, wherein said first contacting terminal is provided at said wall end of said stationary housing and said second contacting terminal is provided at a corresponding edge of said sliding housing and arranged in such a manner that when said bag is disposed at said protection cavity that said liquid is heated below said usable temperature, said sliding housing is slid in said stationary housing to conductively contact said second contacting terminal with said first contacting terminal to ensure an operation of said heating unit to heat up said liquid, and when said bag is expanded to slidably push said such a manner that when said bag is disposed at said protection cavity, said sliding housing out of said stationary housing, said second contacting terminal is moved apart from said first contacting terminal so as to cut off said power supply of said charging unit.

10. The warmer device, as recited in claim 3, wherein said protection device further comprises a supporting platform for supporting said bag thereon, a supporting shaft upwardly extended from said supporting platform, and a pivot arm having a pivot end pivotally coupled with said supporting shaft and a contacting end sitting on top of said bag, wherein said affixing wall and said movable wall are defined at said supporting platform and said pivot arm respectively, such that when said bag is expanded, said pivot arm is pivotally lifted from said supporting platform in response to said expansion of said bag to actuate said actuator for cutting off said power supply of said charging unit.

11. The warmer device, as recited in claim 10, wherein said first contacting terminal is provided on top of said supporting shaft and said second contacting terminal is provided at said pivot end of said pivot arm- and arranged in such a manner that when said bag is disposed on said supporting platform that said liquid is heated below said usable temperature, said pivot arm is pivotally and downwardly sat on said bag to conductively contact said second contacting terminal with said first contacting terminal to ensure an operation of said heating unit to heat up said liquid, and when said bag is expanded to pivotally and upwardly push said arm, said second contacting terminal is moved apart from said first contacting terminal so as to cut off said power supply of said charging unit.

12. The warmer device, as recited in claim 2, wherein said actuator comprises a first contacting terminal provided at said affixing wall and a second contacting terminal provided at said movable wall and arranged in such a manner that when said bag is disposed at said protection cavity that said liquid is heated below said usable temperature, said second contacting terminal is spaced apart from said first contacting terminal to ensure an operation of said heating unit to heat up said liquid, and when said bag is expanded to push said movable wall, said second contacting terminal is conductively contacted with said first contacting terminal so as to cut off said power supply of said charging unit.

13. The warmer device, as recited in claim 12, wherein said affixing wall is affixed in said protection cavity and said movable wall are slidably supported in said protection cavity at a position spaced apart from said affixing wall, in such a manner that when said bag is disposed at said protection cavity that said liquid is heated below said usable temperature, said second contacting terminal is not contacted with said first contacting terminal to ensure an operation of said heating unit to heat up said liquid, and when said bag is expanded to slidably push said movable wall, said second contacting terminal is conductively contacted with said first contacting terminal so as to cut off said power supply of said charging unit.

14. The warmer device, as recited in claim 13, wherein said protection device further comprises a resilient element supported between said affixing wall and said movable wall for applying an urging force against said movable wall to ensure said second contacting terminal being not contacted with said first contacting terminal before said bag is expanded.

15. The warmer device, as recited in claim 3, wherein said heating unit comprises a plurality of heaters supported in said sealed cavity to heat up said liquid and at least a temperature sensor supported adjacent to said power supply of the charging unit to prevent an overheat of said liquid, such that said monitoring device and said heating unit provide dual-safety feature for said bag.

16. The warmer device, as recited in claim 12, wherein said heating unit comprises a plurality of heaters supported in said sealed cavity to heat up said liquid and at least a temperature sensor supported adjacent to said power supply of the charging unit to prevent an overheat of said liquid, such that said monitoring device and said heating unit provide dual-safety feature for said bag.

17. The portable warmer, as recited in claim 15, wherein said heating unit further comprises a signal generator provided at said protection device and electrically coupled with said actuator for generating a notifying signal when said power supply of said charging unit is cut off.

18. The portable warmer, as recited in claim 16, wherein said heating unit further comprises a signal generator provided at said protection device and electrically coupled with said actuator for generating a notifying signal when said power supply of said charging unit is cut off.

19. The portable warmer, as recited in claim 17, wherein said fluid is partially filled in said bag that when said bag is disposed at said protection device, a bottom portion of said bag is filled with said fluid while an upper portion of said bag is filled with gas, wherein said heaters are retained at a position that said heaters are submerged at said fluid to effectively heat up said fluid when said bag is disposed at said protection device.

20. The portable warmer, as recited in claim 18, wherein said fluid is partially filled in said bag that when said bag is disposed at said protection device, a bottom portion of said bag is filled with said fluid while an upper portion of said bag is filled with gas, wherein said heaters are retained at a position that said heaters are submerged at said fluid to effectively heat up said fluid when said bag is disposed at said protection device.

21. An operating method of a warmer device, comprising the steps of:
    receiving a rechargeable warmer bag of said warmer device at a protection cavity of a protection device, wherein a rechargeable warmer bag which comprises a bag defining a sealed cavity and receiving a predetermined of liquid therein;
    charging said rechargeable warmer bag at said protection cavity of said protection device by a charging unit to heat up said liquid at a usable temperature, wherein when said liquid is heated up at said usable temperature, said bag is expanded to increase a size thereof;
    monitoring said rechargeable warmer bag during charging and cutting off a power supply from said charging unit when said rechargeable warmer bag is heated to be expanded to a predetermined extent; and
    enabling said rechargeable warmer bag to be removed and separated from said protection device when said rechargeable warmer bag is fully charged in said protection device.

22. The method, as recited in claim 21, wherein the monitoring step further comprises the steps of:
    configuring an affixing wall and a movable wall at said protection device; and
    providing an actuator on at least one of said affixing wall and said movable wall; and when said bag is expanded, pushing said movable wall in response to an expansion of said bag to actuate said actuator for cutting off said power supply of said charging unit.

23. The method, as recited in claim 22, wherein the step of providing said actuator on at least one of said affixing wall and said movable wall further comprises the steps of:

provantage first and second contacting terminals at said affixing wall and said movable wall respectively, when said bag is disposed at said protection cavity that said liquid is heated below said usable temperature, conductively contacting said second contacting terminal with said first contacting terminal to ensure an operation of said charging unit to heat up said liquid; and when said bag is expanded to push said movable wall, moving said second contacting terminal apart from said first contacting terminal so as to cut off said power supply of said charging unit.

24. The method, as recited in claim 22, wherein the step of providing said actuator on at least one of said affixing wall and said movable wall further comprises the steps of:

providing first and second contacting terminals at said affixing wall and said movable wall respectively, when said bag is disposed at said protection cavity that said liquid is heated below said usable temperature, spacing said second contacting terminal apart said first contacting terminal that said second contacting terminal is not contact with said first contacting terminal to ensure an operation of said charging unit to heat up said liquid; and when said bag is expanded to push said movable wall, conductively contacting said second contacting terminal with said first contacting terminal so as to cut off said power supply of said charging unit.

* * * * *